United States Patent

Tsubata et al.

(10) Patent No.: US 6,194,444 B1
(45) Date of Patent: Feb. 27, 2001

(54) 1,2,3-THIADIAZOLE DERIVATIVES OR SALTS THEREOF AND AGROHORTICULTURAL DISEASE CONTROLLER AND METHOD FOR USING THE SAME

(75) Inventors: Kenji Tsubata, Kawachinagano; Takashi Shimaoka, Sakai; Osamu Sampei, Kawachinagano; Yoshitaka Taniyama, Funabashi; Kazuhiro Takagi, Osaka; Tsutomu Nishiguchi, Kawachinagano; Sohkichi Tajima, Osaka, all of (JP)

(73) Assignee: Nihon Nohyaku Co., LTD, Tokyo (JP)

( * ) Notice: Subject to any disclaimer, the term of this patent is extended or adjusted under 35 U.S.C. 154(b) by 0 days.

(21) Appl. No.: 09/276,705

(22) Filed: Mar. 26, 1999

Related U.S. Application Data

(63) Continuation of application No. PCT/JP97/03467, filed on Sep. 29, 1997.

(30) Foreign Application Priority Data

Sep. 30, 1996 (JP) .................................................. 8-278948

(51) Int. Cl.⁷ .................................................. A01N 43/828
(52) U.S. Cl. ........................................... 514/361; 548/127
(58) Field of Search ............................. 548/127; 514/361

(56) References Cited

U.S. PATENT DOCUMENTS

| | | |
|---|---|---|
| 3,914,121 | 10/1975 | Doyle . |
| 3,970,652 | 7/1976 | Doyle . |
| 4,177,054 | 12/1979 | Arndt et al. . |
| 4,914,097 | 4/1990 | Oda et al. . |
| 4,956,375 | 9/1990 | Oda et al. . |
| 5,073,563 * | 12/1991 | Frickel .................. 514/365 |
| 5,098,918 * | 3/1992 | Thomas .................. 514/361 |
| 5,227,392 | 7/1993 | Frickel et al. . |

FOREIGN PATENT DOCUMENTS

| | | |
|---|---|---|
| 947297 | 10/1975 | (CA) . |
| 280275 | 2/1988 | (EP) . |
| 889033 | 9/1996 | (EP) . |
| 70-27573 | 9/1970 | (JP) . |
| 50-049271 * | 5/1975 | (JP) .................................................. 548/127 |
| 54-9272 | 1/1979 | (JP) . |
| 63-258868 | 10/1988 | (JP) . |
| 2-175 | 1/1990 | (JP) . |
| 2-149579 | 6/1990 | (JP) . |
| 3-181463 | 8/1991 | (JP) . |
| 4-234881 | 8/1992 | (JP) . |
| 7-252242 | 10/1995 | (JP) . |
| 9-249665 | 9/1997 | (JP) . |
| WO95/01340 | 1/1995 | (WO) . |
| WO 95/07278 | 3/1995 | (WO) . |
| 0707000 | 4/1996 | (WO) . |
| WO96/29871 | 10/1996 | (WO) . |
| WO 97/12863 | 4/1997 | (WO) . |

\* cited by examiner

Primary Examiner—Robert Gerstl

(57) ABSTRACT

A 1,2,3-thiadiazole derivative represented by general formula (I) or a salt thereof:

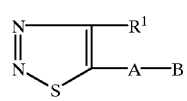

(I)

wherein $R^1$ is H, (halo) $C_1$–$C_4$ alkyl, 5- or 6-membered heterocycle containing 1 to 3 same or different O, N or S, A is a group of the following formulas:

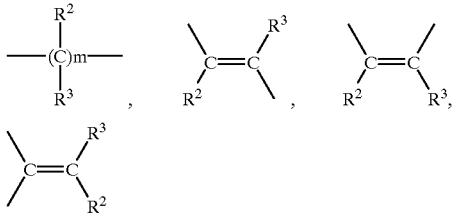

wherein $R^2$ and $R^3$ are H, halogen, cyano, formyl, alkylthio, alkoxycarbonyl, substituted or unsubstituted phenyl, B is cyano or an unsubstituted or substituted 5- or 6-membered heterocycle containing 1–3 hetero atoms selected from O, N and S, and m is 0–4; an agrohorticultural disease controller containing said derivative.

4 Claims, No Drawings

1,2,3-THIADIAZOLE DERIVATIVES OR SALTS THEREOF AND AGROHORTICULTURAL DISEASE CONTROLLER AND METHOD FOR USING THE SAME

This is a Continuation of International Application No. PCT/JP97/03467 filed Sep. 29, 1997 which designated the U.S.

TECHNICAL FIELD

The present invention relates to 1,2,3-thiadiazole derivatives and salts thereof, and agrohorticultural disease controller containing said compound as an active ingredient, and method for using the disease controller.

BACKGROUND ART 1,2,3-Thiadiazoles are disclosed in JP-A-2-149579/1990 as an agent for treating central nervous system diseases, in JP-A-54-9272/1979, JP-A-3-181463/1991, JA-A-4-234881/1992, Canadian Patent 947297, etc. as a herbicide or a plant growth regulator, and in WO 9501340 and JP-A-7-252242/1995 as a fungicide.

DISCLOSURE OF THE INVENTION

With the aim of creating a novel agrohorticultural disease controller, the present inventors have conducted extensive studies to find that the 1,2,3-thiadiazole derivatives of the present invention represented by general formula (I) or salts thereof which are novel compounds not found in literature are useful as an agrohorticultural disease controller. Based on this finding, the present invention has been accomplished.

The present invention relates to 1,2,3-thiadiazole derivatives represented by the following general formula (I) or salts thereof, an agrohorticultural disease controller containing said compounds as an active ingredient, and a method for using said disease controller:

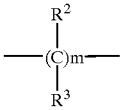

(I)

wherein $R^1$ represents hydrogen atom, $C_1$–$C_8$ alkyl group, halo $C_1$–$C_4$ alkyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_1$ alkyl group, $C_1$–$C_4$ alkoxy group, halo $C_1$–$C_4$ alkoxy group and $C_1$–$C_4$ alkoxycarbonyl group, 5- or 6-membered heterocycle containing 1 to 3 same or different heteroatoms selected from oxygen atom, nitrogen atom and sulfur atom, or substituted 5- or 6-membered heterocycle containing 1 to 3 same or different heteroatoms selected from oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, carboxy $C_1$–$C_4$ alkoxycarbonyl $C_1$–$C_4$ alkyl group, amino group, substituted amino group having 1 or 2 same or different substituents selected from the group consisting of $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups;

A represents a group of the following formula:

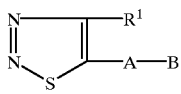

(wherein $R^2$ and $R^3$, same or different, represent hydrogen atom, halogen atom, cyano group, formyl group, $C_1$–$C_4$ alkyl group, $C_1$–$C_4$ alkoxy group, $C_1$–$C_4$ alkylthio group, $C_1$–$C_4$ alkylsulfinyl group, $C_1$–$C_4$ alkylsulfonyl group, $C_1$–$C_4$ alkylcarbonyl group, $C_1$–$C_4$ alkoxycarbonyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group and $C_1$–$C_4$ alkoxycarbonyl group, phenylcarbonyl group, or substituted phenylcarbonyl group having, on the ring thereof, 1 to 5 same or different substituents selected from the group consisting of halogen atom, hydroxyl group, cyano group, $C_1$–$C_4$ alkyl group and $C_1$–$C_4$ alkoxycarbonyl group; further, $R^2$ and $R^3$ may be taken conjointly to form a 3- to 7-membered ring including a $C_2$–$C_6$ alkylene group which may be intercepted by —O—,
—S($O)_n$—in which n is an integer of 0 to 2,
—CO— or
—$NR^8$— in which $R^8$ represents hydrogen atom, formyl group, $C_1$–$C_8$ alkyl group, halo $C_1$–$C_4$ alkyl group, $C_2$–$C_4$ alkenyl group, halo $C_2$–$C_4$ alkenyl group, $C_2$–$C_4$ alkynyl group, halo $C_2$–$C_4$ alkynyl group, $C_1$–$C_4$ alkylthio group, $C_1$–$C_4$ alkylsulfinyl group, $C_1$–$C_4$ alkylsulfonyl group, $C_1$–$C_4$ alkylcarbonyl group, $C_1$–$C_4$ alkoxycarbonyl group, carbamoyl group, substituted carbamoyl group having 1 or 2 same or different substituents selected from the group consisting of $C_1$–$C_4$ alkyl group and phenyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenyl $C_1$–$C_4$ alkyl group, substituted phenyl $C_1$–$C_4$ alkyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenylcarbonyl group, or substituted phenylcarbonyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group; and said 3- to 7-membered ring may be substituted by one or more same or different substituents selected from the group consisting of halogen atom and $C_1$–$C_4$ alkyl group; and m represents an integer of 0 to 4), or

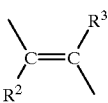

in which $R^2$ and $R^3$ are as defined above, or

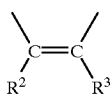

in which $R^2$ and $R^3$ are as defined above, or

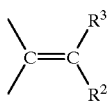

in which $R^2$ and $R^3$ are as defined above; and in the case that m is 0 in the definition of A, B represents cyano group, 5- or 6-membered heterocycle having 1 to 3 same or different hetero atoms selected from the group consisting of oxygen atom, nitrogen atom and sulfur atom, substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different $C_1$–$C_4$ alkyl or phenyl groups, carbamoyl group, substituted carbamoyl group having 1 or 2 $C_1$–$C_4$ alkyl or phenyl groups, carbamoyl $C_1$–$C_4$ alkyl group and substituted carbamoyl $C_1$–$C_4$ alkyl group having 1 or 2 same or different $C_1$–$C_4$ alkyl or phenyl groups, or

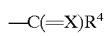

(in which $R^4$ represents hydrogen atom, $C_1$–$C_8$ alkyl group, halo $C_1$–$C_4$ alkyl group, $C_2$–$C_4$ alkenyl group, halo $C_2$–$C_4$ alkenyl group, $C_2$–$C_4$ alkynyl group, halo $C_2$–$C_4$ alkynyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenyl $C_1$–$C_4$ alkyl group, substituted phenyl $C_1$–$C_4$ alkyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, 5- or 6-membered heterocycle containing 1 to 3 same or different hetero atoms selected from the group consisting of oxygen atom, nitrogen atom and sulfur atom, or substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl group and phenyl group, carbamoyl group, substituted carbamoyl group having 1 or 2 same or different substituents selected from the group consisting of $C_1$–$C_4$ alkyl group and phenyl group, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl group and phenyl group, and X represents O, S, N—$R^6$ in which $R^6$ is as defined later, NO—$R^6$ in which $R^6$ is as defined later, N(→O)—$R^6$ in which $R^6$ is as defined later, NN($R^6$)$R^7$ in which $R^6$ and $R^7$ are as defined later, or NN=C($R^6$)$R^7$ (in which $R^6$ and $R^7$, same or different, represent hydrogen atom, halogen atom, formyl group, $C_1$–$C_4$ alkyl group, $C_2$–$C_4$ alkenyl group, $C_2$–$C_4$ alkynyl group, $C_1$–$C_4$ alkylsulfonyl group, halo $C_1$–$C_4$ alkylsulfonyl group, $C_1$–$C_{20}$ alkylcarbonyl group, $C_1$–$C_4$ alkoxycarbonyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group, amino group and $C_1$–$C_4$ alkoxycarbonyl group, phenyl $C_1$–$C_4$ alkyl group, substituted phenyl $C_1$–$C_4$ alkyl group having, on the ring thereof, 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group, amino group and $C_1$–$C_4$ alkoxycarbonyl group, phenylcarbonyl group, substituted phenylcarbonyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group and $C_1$–$C_4$ alkoxycarbonyl group, carbamoyl group, substituted carbamoyl group having 1 or 2 same or different substituents selected from the group consisting of $C_1$–$C_4$ alkyl group, phenyl group and substituted phenyl group having, on the ring thereof, 1 to 5 same or different substituents selected from the group consisting of halogen atom, $C_1$–$C_4$ alkyl group, halo $C_1$–$C_4$ alkyl group, $C_1$–$C_4$ alkoxy group and halo $C_1$–$C_4$ alkoxy group, phenylsulfonyl group, substituted phenylsulfonyl group having 1 to 5 same or different substituents selected from the group consisting of halogen atom, hydroxyl group, cyano group, nitro group, $C_1$–$C_4$ alkyl group, $C_1$–$C_4$ alkoxy group and $C_1$–$C_4$ alkoxycarbonyl group, thiocarbamoyl group, substituted thiocarbamoyl group substituted by same or different $C_1$–$C_4$ alkyl or phenyl group, $C_1$–$C_4$ alkoxy carbonimidoyl group, substituted $C_1$–$C_4$ alkoxy carbonimidoyl group having, on the nitrogen atom thereof, same or different substituents selected from the group consisting of $C_1$–$C_4$ alkyl and phenyl groups, $C_1$–$C_4$ alkylthio carbonimidoyl group, substituted $C_1$–$C_4$ alkylthio carbonimidoyl group having, on the nitrogen atom thereof, same or different substituents selected from the group consisting of $C_1$–$C_4$ alkyl and phenyl groups, $C_1$–$C_4$ alkylsulfinyl carbonimidoyl group, substituted $C_1$–$C_4$ alkylsulfinyl carbonimidoyl group having, on the nitrogen atom thereof, same or different substituents selected from the group consisting of $C_1$–$C_4$ alkyl and phenyl groups, $C_1$–$C_4$ alkylsulfonyl carbonimidoyl group, substituted $C_1$–$C_4$ alkysulfonyl carbonimidoyl group having, on the nitrogen atom thereof, same or different substituents selected from the group consisting of $C_1$–$C_4$ alkyl and phenyl groups, amidino group, substituted amidino group having same or different substituents selected from the group consisting of $C_1$–$C_6$ alkyl and phenyl groups, 5- or 6-membered heterocycle containing 1 to 3 same or different hetero atoms selected from the group consisting of oxygen atom, nitrogen atom and sulfur atom, or substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups; and $R^6$ and $R^7$ may be taken conjointly to form a 3- to 7-membered ring including a $C_2$–$C_6$ alkylene group which may be intercepted by —O—,
—S(O)$_n$— in which n is as defined above,
—CO—, or
—NR$^8$— in which $R^8$ is as defined above, and said 3- to 7-membered ring may have same or different substituents selected from the group consisting of halogen atom and $C_1$–$C_4$ alkyl group)); and in cases where m is 1 or greater, B represents hydrogen atom, halogen atom, cyano group, 5- or 6-membered heterocycle containing 1 to 3 same or different hetero atoms selected from the group consisting of oxygen atom, nitrogen atom and sulfur atom, substituted 5- or 6-membered heterocycle containing 1 to 3 same or different hetero atoms selected from the group consisting of oxygen atom, nitrogen atom and sulfur atom and having 1 to 3 same or different substituents selected from the group consisting of halogen atom, hydroxyl group, cyano group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups,

—C(=X)R$^5$ (in which X is as defined above; and $R^5$ represents hydrogen atom, $C_1$–$C_8$ alkyl group, halo $C_1$–$C_4$ alkyl group, $C_2$–$C_4$ alkenyl group, halo $C_2$–$C_4$ alkenyl group, $C_2$–$C_4$ alkynyl group, halo $C_2$–$C_4$ alkynyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenyl $C_1$–$C_4$ alkyl group, substituted phenyl $C_1$–$C_4$ alkyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, 5- to 6-membered heterocycle containing 1 to 3 same or different hetero atoms selected from the group consisting of oxygen atom, nitrogen atom and sulfur atom, substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups, O—R$^6$ in which $R^6$ is as defined above,
S(O)$_n$—R$^6$ in which n and $R^6$ are as defined above, or
N(R$^6$)R$^7$ in which $R^6$ and $R^7$ are as defined above),

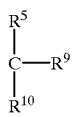

(wherein $R^5$ is as defined above; and $R^9$ and $R^{10}$, same or different, represent formyl group, $C_1$–$C_4$ alkylcarbonyl group, $C_1$–$C_4$ alkoxycarbonyl group, phenylcarbonyl group, or substituted phenylcarbonyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group; further, $R^9$ and $R^{10}$ may be taken conjointly to form a 3- to 7-membered ring including a $C_2$ to $C_6$ alkylene group which may be intercepted by —O—,
—S(O)$_n$— in which n is as defined above,
—CO—, or
—N(R$^8$)— in which $R^8$ is as defined above, and said 3- to 7-membered ring may have one or more same or different substituents selected from the group consisting of halogen atom and $C_1$–$C_4$ alkyl group), O—R$^6$ in which $R^6$ is as defined above,
S(O)$_n$—R$^6$ in which $R^6$ and n are as defined above,
N(R$^6$)R$^7$ in which $R^6$ and $R^7$ are as defined above,
N=C(R$^6$)R$^7$ in which $R^6$ and $R^7$ are as defined above, or
ON=C(R$^6$)R$^7$ in which $R^6$ and $R^7$ are as defined above.

BEST MODE FOR CARRYING OUT THE INVENTION

In the definitions of the substituents in the 1,2,3-thiadiazole derivatives of the present invention represented by general formula (I), the term "halogen atom" means chlorine atom, bromine atom, iodine atom or fluorine atom; the term "$C_1$–$C_8$ alkyl group" means a straight or branched chain alkyl group having 1 to 8 carbon atoms such as methyl, ethyl, n-propyl, i-propyl, n-butyl, i-butyl, s-butyl, t-butyl, n-pentyl, n-hexyl, n-heptyl, n-octyl and the like; the term "halo $C_1$–$C_4$ alkyl group" means a straight or branched chain alkyl group having 1 to 4 carbon atoms and substituted by one or more same or different halogen atoms, the term "$C_2$–$C_4$ alkenyl group" means a straight or branched chain alkenyl group having 2 to 4 carbon atoms and a double bond, and the term "halo $C_2$–$C_4$ alkenyl group" means a straight or branched chain alkenyl group having 2 to 4 carbon atoms and substituted by at least one same or different halogen atom.

The term "$C_2$–$C_4$ alkynyl group" means a straight or branched chain alkynyl group having 2 to 4 carbon atoms and a triple bond, the term "halo $C_2$–$C_4$ alkynyl group" means a straight or branched chain alkynyl group having 2 to 4 carbon atoms and substituted by one or more same or different halogen atoms, and the term "5- or 6-membered heterocycle containing at least one same or different hetero atoms selected from the group consisting of oxygen atom, nitrogen atom and sulfur atom" means a 5- or 6-membered ring such as furan, thiophene, pyrrole, oxazole, thiazole, isothiazole, pyrazole, imidazole, 1,2,3-thiadiazole, 1,2,4-thiadiazole, 1,2,5-thiadiazole, 1,3,4-thiadiazole, 1,2,4-triazole, pyridine, pyridazine, pyrimidine, pyrazine, pyrrolidine, piperidine, morpholine, thiomorpholine, dithiolane, dithiane, piperazine, dioxolane, imidazolidine and the like.

As examples of the salt of 1,2,3-thiadiazole derivative represented by general formula (I), there can be referred to salts of alkali metals such as sodium, potassium and the like, salts of alkaline earth metals such as calcium, magnesium and the like, ammonium salts, substituted ammonium salts substituted by one or more same or different substituents selected from the group consisting of $C_1$–$C_{12}$ alkyl group, phenyl group, substituted phenyl group, benzyl group or substituted benzyl group, guanidium salt and the like.

As preferred substituents of the present invention, the following are referred to. Thus, as $R^1$, methyl, ethyl, n-propyl, cyclopropyl and the like are preferred. As A, a single bond (B is directly linked to thiadiazole ring) or methylene are preferred. In a case where A is a single bond, B is preferably cyano, formyl, hydroxyiminomethyl, benzyloxyiminomethyl, hydrazonomethyl, phenylhydrazonomethyl, imidazolin-2-yl, 4-methylthiazol-2-yl and the like. In a case where A is methylene, B is preferably chlorine atom, hydroxyl group, methoxy group, benzyloxy group, acetoxy group, benzoyloxy group, ethoxycarbonyloxy group, amino group and hydrochloride thereof, diethylamino group, dipropenylamino group, benzoylamino group, p-toluenesulfonylamino group, 3-phenylureido group, 4-methl-1,2,3-thiadiazol-5-ylmethoxy group and the like.

The 1,2,3-thiadiazole derivatives of the present invention represented by general formula (I) and salts thereof can be produced, for example, by the Production processes exemplified below.

Production process 1

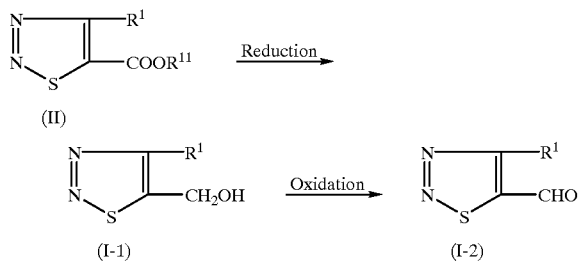

wherein $R^1$ is as defined above and $R^{11}$ represents $C_1$–$C_8$ alkyl group.

A 1,2,3-thiadiazole derivative represented by general formula (I-1) can be produced by reducing a compound of general formula (II) in the presence of a reductant to form a 1,2,3-thiadiazole derivative represented by general formula (I-1) and, after isolating or without isolating the thus formed (I-1), oxidizing (I-1) in the presence of an oxidant.

This reaction can be performed according to the description of Shin Jikken Kagaku Koza, Vol. 15 (II), p. 191 (Maruzen K. K.); Jikken Kagaku Koza (4th edition), Vol. 23(V), p. 43 (Maruzen K. K.), etc.

Production process 2

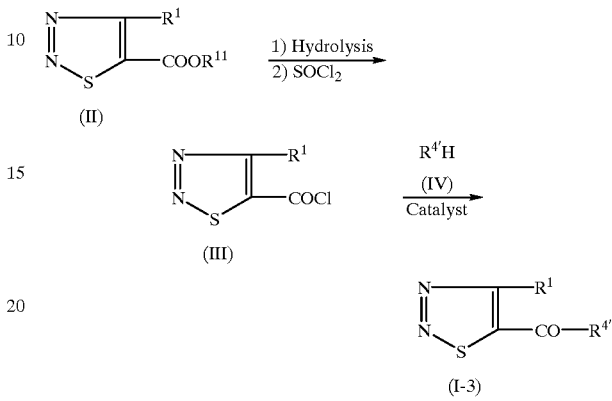

wherein $R^1$ and $R^{11}$ are as defined above, and $R^{4'}$ represents phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, 5- or 6-membered heterocycle containing 1 to 3 same or different hetero atoms selected from the group consisting of oxygen atom, nitrogen atom and sulfur atom, or substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups.

A 1,2,3-thiadiazole derivative represented by general formula (I-3) can be produced by hydrolyzing a compound of general formula (II) and then reacting it with thionyl chloride to form a compound represented by general formula (III), and after isolating compound (III) or without isolating (III), reacting (III) with a compound of general formula (IV) in the presence of a catalyst.

This reaction can be performed according to the description of "Shin Jikken Kagaku Koza", Vol. 14(II), p. 794.

Production process 3

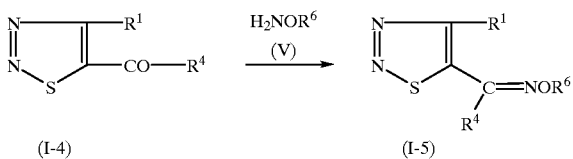

wherein $R^1$, $R^4$ and $R^6$ are as defined above.

A 1,2,3-thiadiazole derivative represented by general formula (I-5) can be produced by reacting a 1,2,3-thiadiazole derivative of general formula (I-4) with a compound represented by general formula (V).

This reaction can be performed according to the description of "Jikken Kagaku Koza" (4th edition), Vol. 20 (V), p. 353.

Production process 4

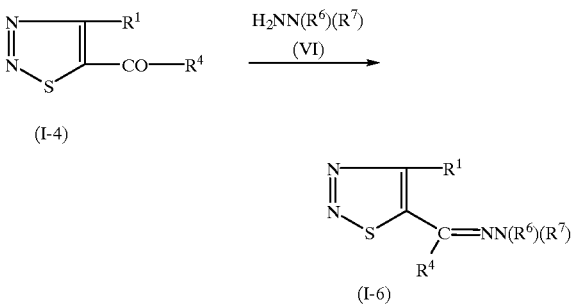

wherein $R^1$, $R^4$, $R^6$ and $R^7$ are as defined above.

A 1,2,3-thiadiazole derivative represented by general formula (I-6) can be produced by reacting a 1,2,3-thiadiazole derivative of general formula (I-4) with a compound represented by general formula (VI).

This reaction can be performed according to the description of Org. Synth. Coll. VI, p.12 (1988).

Production process 5 wherein $R^1$ and $R^6$ are as defined above and Hal represents halogen atom.

A 1,2,3-thiadiazole derivative represented by general formula (I-8) or (I-9) can be produced by treating a 1,2,3-thiadiazole derivative represented by general formula (I-1) with a halogenating agent such as thionyl chloride or phosphorus tribromide to form a compound represented by general formula (III'), and after isolating the compound (III') or without isolating (III'), reacting the compound (III') with sodium formimide and then with an acid such as hydrochloric acid to form a salt of a 1,2,3-thiadiazole derivative represented by general formula (I-7), and then reacting the salt (I-7) with a compound of formula (VII). Further, if a salt of the 1,2,3-thiadiazole derivative of formula (I-7) is reacted with an isocyanate of formula (VIII), a 1,2,3-thiadiazole derivative of general formula (I-8') can be obtained.

This reaction can be performed according to the description of "Jikken Kagaku Koza" (4th edition), Vol. 19 (I), p. 438; Synthesis, 615 (1990); "Jikken Kagaku Koza" (4th edition), Vol. 22 (II), p. 1142; "Shin Jikken Kagaku Koza", Vol. 14 (III), p. 1631; etc.

Production process 6

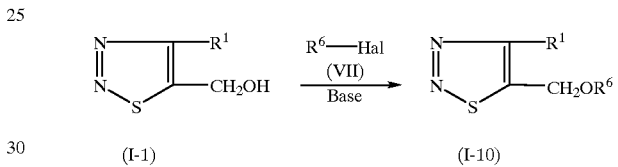

wherein $R^1$, $R^6$ and Hal are as defined above.

A 1,2,3-thiadiazole derivative represented by general formula (I-10) can be produced by reacting a 1,2,3-thiadiazole derivative of formula (I-1) with a compound represented by formula (VII) in the presence of a base.

This reaction can be performed according to the description of "Jikken Kagaku Koza" (4th edition), Vol. 22 (V), p..50.

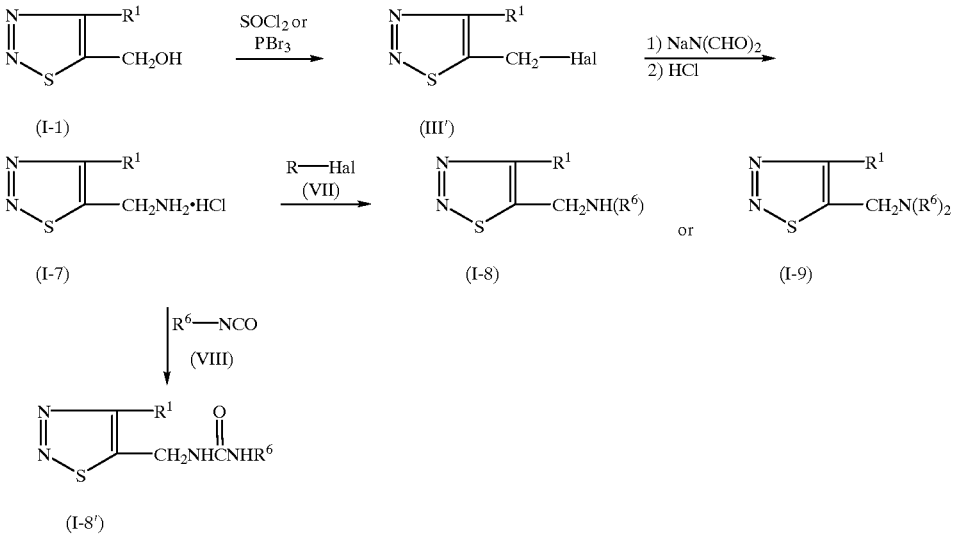

Production process 7

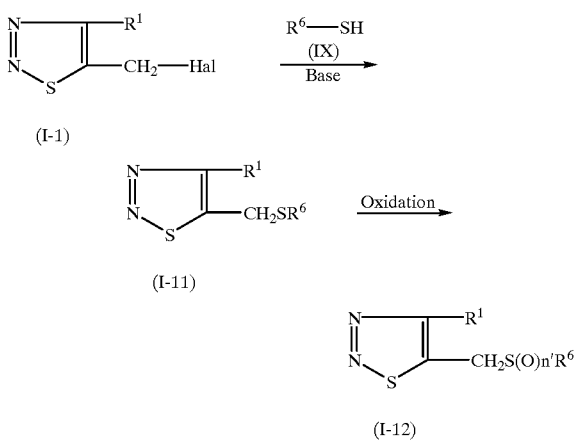

wherein $R^1$, $R^6$ and Hal are as defined above and n' represents an integer of 1–2.

A 1,2,3-thiadiazole derivative represented by general formula (I-12) can be produced by reacting a 1,2,3-thiadiazole derivative of general formula (I-1) with a compound represented by general formula (IX) in the presence of a base to form a 1,2,3-thiadiazole derivative represented by general formula (I-11), and after isolating the compound (I-11) or without isolation it, oxidizing the derivative (I-11) in the presence of an oxidant.

This reaction can be performed according to the description of "Shin Jikken Kagaku Koza", Vol. 14 (III), p. 1716; "Jikken Kagaku Koza" (4th edition), Vol. 24 (VI), p. 365; etc.

Production process 8

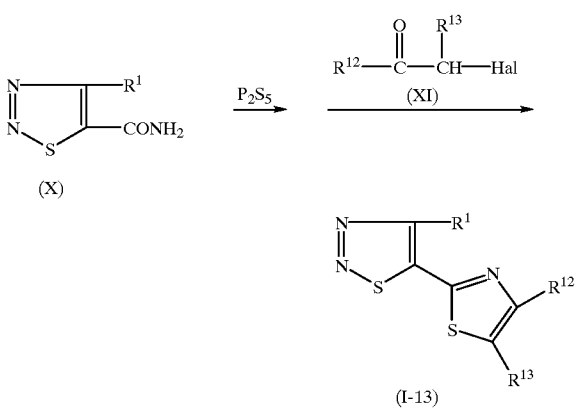

wherein $R^1$ and Hal are as defined above; and $R^{12}$ and $R^{13}$, same or different, represent $C_1$–$C_4$ alkyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, carbamoyl group, substituted carbamoyl having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups.

A 1,2,3-thiadiazole derivative represented by general formula (I-13) can be produced by reacting a compound represented by general formula (X) with phosphorus pentasulfide and then with a compound represented by general formula (XI).

This reaction can be performed according to the description of "Shin Jikken Kagaku Koza", Vol. 14 (IV), p. 2198; Org. Synth., Coll. Vol. III, p. 332 (1955); etc.

Production process 9

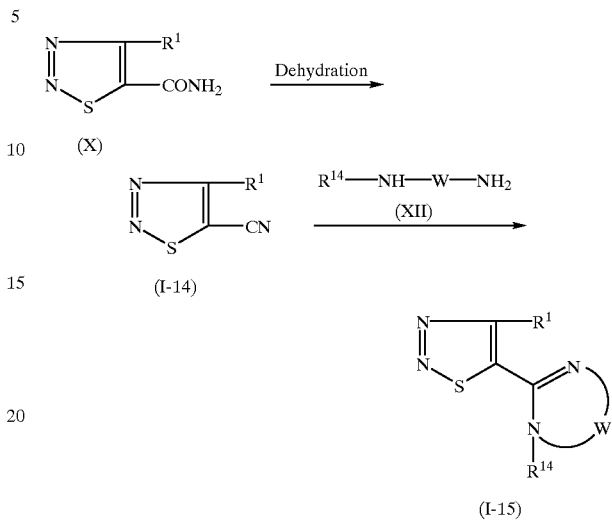

wherein $R^1$ is as defined above, $R^{14}$ represents hydrogen atom or $C_1$–$C_4$ alkyl, and W represents $C_3$–$C_6$ alkylene group which may be substituted by $C_1$–$C_4$ alkyl group and may be intercepted by
—O—,
—$NR^6$— in which $R^6$ is as defined above,
—S(O)$_n$— in which n is as defined above, or
—CO—.

A 1,2,3-thiadiazole derivative represented by general formula (I-15) can be produced by subjecting a compound of general formula (X) to a dehydrating reaction to form a 1,2,3-thiadiazole derivative represented by general formula (I-14), and after isolating the derivative (I-14) or without isolating it, reacting the derivative (I-14) with a compound represented by general formula (XII).

This reaction can be performed according to the description of "Shin Jikken Kagaku Koza", Vol. 14 (II), p. 1190.

Production process 10

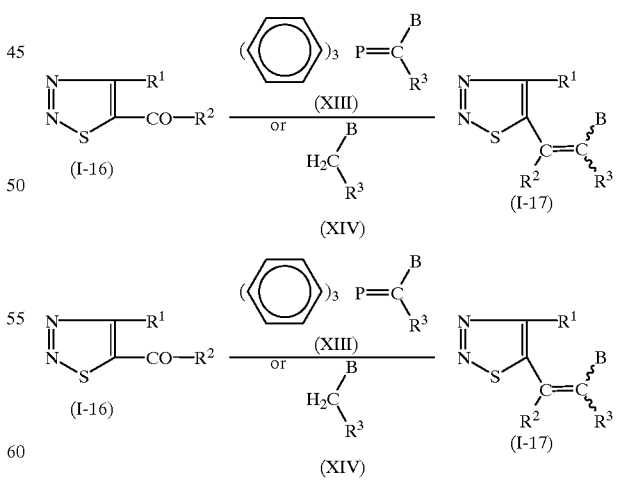

wherein $R^1$, $R^2$, $R^3$ and B are as defined above.

A 1,2,3-thiadiazole derivative represented by general formula (I-17) can be produced by reacting a 1,2,3-thiadiazole derivative represented by general formula (I-16) with a compound represented by formula (XIII) or formula (XIV).

This reaction can be performed according to the description of "Shin Jikken Kagaku Koza", Vol. 14 (I), p. 224; JP-A-7-165757/1995; etc.

The compound of general formula (II) used as a starting compound for production of the 1,2,3-thiadiazine derivative represented by general formula (I) can be produced, for example, by the following method.

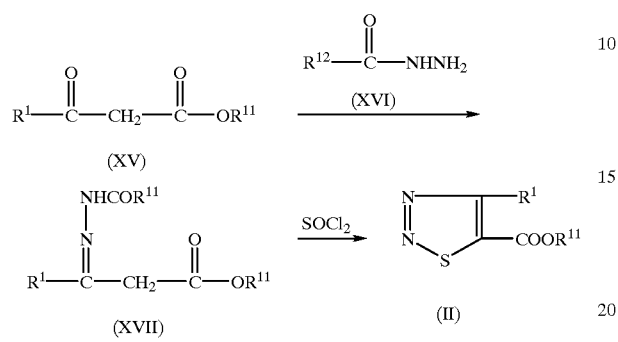

wherein $R^1$ is as defined above, $R^{11}$ represents $C_1$–$C_8$ alkyl group, and $R^{12}$ represents $C_1$–$C_4$ alkyl group, $C_1$–$C_4$ alkoxy group or amino group which may have a substituent.

A compound represented by general formula (II) can be produced by reacting a compound represented by general formula (XV) with a compound represented by general formula (XVI) to form a compound represented by general formula (XVII), and after isolating the compound (XVII) or without isolating it, subjecting the compound (XVII) to ring closure using thionyl chloride.

This reaction can be preformed according to the description of J. Am. Chem. Soc., 77, 5359 (1955), etc.

Next, typical examples of the 1,2,3-thiadiazole derivative of the present invention represented by general formula (I) are mentioned below. The invention is by no means limited by these examples.

In Table 1, meaning of the abbreviations are as follows.
Ph: phenyl group
cyclo: alicyclic hydrocarbon

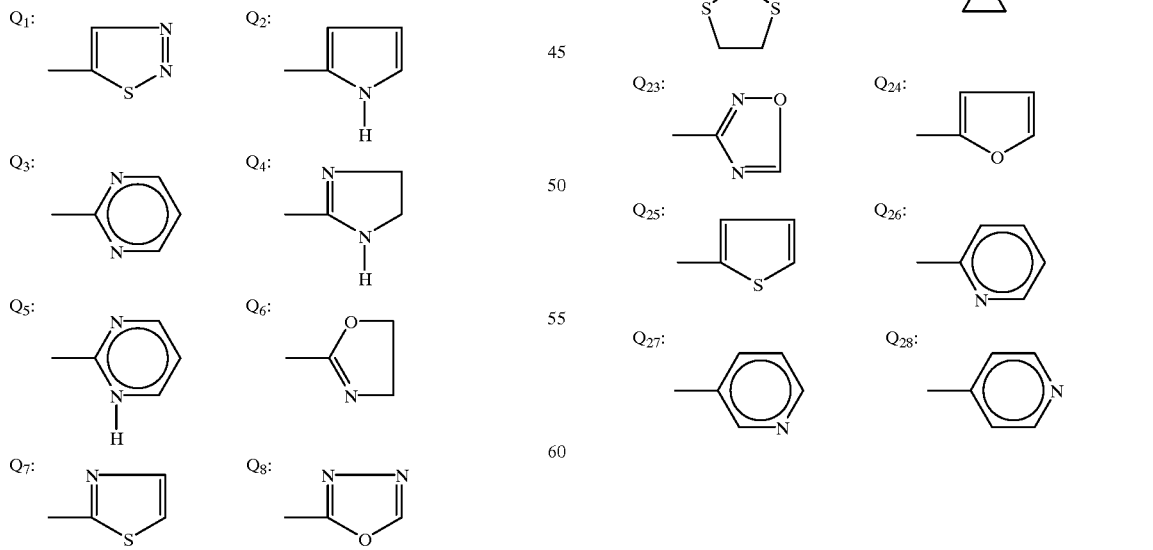

TABLE 1

General formula (I)

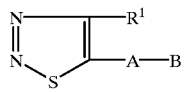

(I)

| No | R¹ | A | B | Property |
|---|---|---|---|---|
| 1 | H | — | COPh | m.p. 60–61° C. |
| 2 | H | $CH_2$ | Cl | |
| 3 | H | $CH_2$ | OH | |
| 4 | H | $CH_2$ | $OCH_3$ | |
| 5 | H | $CH_2$ | $OCH_2Ph$ | |
| 7 | $CH_3$ | — | CHO | nD 1.5555(26° C.) |
| 8 | $CH_3$ | — | $COCH_3$ | |
| 9 | $CH_3$ | — | COPh | nD 1.6145(22° C.) |
| 10 | $CH_3$ | — | CO(2-Cl-Ph) | |
| 11 | $CH_3$ | — | CO(4-Cl-Ph) | |
| 12 | $CH_3$ | — | CO(2-$CH_3$-Ph) | |
| 13 | $CH_3$ | — | CO(4-$CH_3$-Ph) | |
| 14 | $CH_3$ | — | CO(4-i-$C_3H_7$-Ph) | |
| 15 | $CH_3$ | — | CO(4-$CH_3$O-Ph) | |
| 16 | $CH_3$ | — | CO(4-t-$C_4H_9$-Ph) | |
| 17 | $CH_3$ | — | CO-(1-$CH_3$—$Q_2$) | m. p. 85–90° C. |
| 18 | $CH_3$ | — | CN | m. p. 50.4° C. |
| 19 | $CH_3$ | — | CH=NOH | m. p. 270° C.(dec.) |
| 20 | $CH_3$ | — | CH=$NOCH_3$ | m. p. 97° C. |
| 21 | $CH_3$ | — | CH=$NOCH_2Ph$ | nD 1.5998(25° C.) |
| 22 | $CH_3$ | — | CH=$NOCH_2$(2-Cl-Ph) | |
| 23 | $CH_3$ | — | CH=$NOCH_2$(3-Cl-Ph) | |
| 24 | $CH_3$ | — | CH=$NOCH_2$(4-Cl-Ph) | m. p. 70–80° C. |
| 25 | $CH_3$ | — | CH=$NOCH_2$(2-$CH_3$-Ph) | |
| 26 | $CH_3$ | — | CH=$NOCH_2$(3-$CH_3$-Ph) | |
| 27 | $CH_3$ | — | CH=$NOCH_2$(4-$CF_3$-Ph) | |
| 28 | $CH_3$ | — | CH=$NOCH_2$(4-OH-Ph) | |
| 29 | $CH_3$ | — | CH=$NOCH_2$(4-$CH_3$O-Ph) | |
| 30 | $CH_3$ | — | CH=$NOCH_2$(4-$CF_3$O-Ph) | |
| 31 | $CH_3$ | — | CH=$NOCH_2$(4-$NH_2$-Ph) | |
| 32 | $CH_3$ | — | CH=$NOCH_2$(4-$NO_2$-Ph) | |
| 33 | $CH_3$ | — | CH=$NOCH_2$(4-CN-Ph) | |
| 34 | $CH_3$ | — | CH=$NOCH_2$(4-$COOCH_3$-Ph) | |
| 35 | $CH_3$ | — | CH=$NNH_2$ | m. p. 81° C. |
| 36 | $CH_3$ | — | CH=$NNHCH_3$ | |
| 37 | $CH_3$ | — | CH=NNHPh | m. p. 218° C. |
| 38 | $CH_3$ | — | CH=NNH(2-Cl-Ph) | |
| 39 | $CH_3$ | — | CH=NNH(2-F-4-Cl-Ph) | |
| 40 | $CH_3$ | — | CH=NNH(3,5-$Cl_2$-Ph) | |
| 41 | $CH_3$ | — | CH=NNH(3-Cl-Ph) | |
| 42 | $CH_3$ | — | CH=NNH(3-i-$C_3H_7$C-Ph) | |
| 43 | $CH_3$ | — | CH=NNH(4-$CF_3$-Ph) | |
| 44 | $CH_3$ | — | CH=NNH(4-Cl-Ph) | |
| 45 | $CH_3$ | — | CH=$NNHCOOCH_3$ | |
| 46 | $CH_3$ | — | CH=$NNHCOOC_4H_9$-t | |
| 47 | $CH_3$ | — | CH=$NNHCONHCH_3$ | |
| 48 | $CH_3$ | — | CH=$NNHCONHC_2H_5$ | |
| 49 | $CH_3$ | — | CH=NNHCON($CH_3$)Ph | |
| 50 | $CH_3$ | — | CH=NNHCONH(4-Cl-Ph) | |
| 51 | $CH_3$ | — | CH=NNHCONH(4-t-$C_4H_9$-Ph) | |
| 52 | $CH_3$ | — | CH=NNHCONH(4-$CF_3$-Ph) | |
| 53 | $CH_3$ | — | CH=NNHCONH(4-i-$C_3H_7$C-Ph) | |
| 54 | $CH_3$ | — | CH=NNHCONH(4-$CF_3$C-Ph) | |
| 55 | $CH_3$ | — | CH=$NNHCSNHCH_3$ | |
| 56 | $CH_3$ | — | CH=NNHC(N($CH_3$)$_2$)=$NCH_3$ | |
| 57 | $CH_3$ | — | CH=NNHC($CCH_3$)=$NCH_3$ | |
| 58 | $CH_3$ | — | CH=NNHC($SCH_3$)=$NCH_3$ | |
| 59 | $CH_3$ | — | CH=NNHC($SCCH_3$)=$NCH_3$ | |
| 60 | $CH_3$ | — | CH=NNH-(4,6-($CH_3$)$_2$—$Q_3$) | m. p. 182–183° C. |
| 61 | $CH_3$ | — | C(Ph)=NOH | m. p. 172° C. |
| 62 | $CH_3$ | — | C(Ph)=$NOCH_3$ | nD 1.5905(22.8°C.) |
| 63 | $CH_3$ | — | C(Ph)=$NOC_8H_{17}$ | |
| 64 | $CH_3$ | — | C(Ph)=$NOCH_2CH$=$CH_2$ | |
| 65 | $CH_3$ | — | C(Ph)=$NOCH_2CCl$=$CH_2$ | |
| 66 | $CH_3$ | — | C(Ph)=$NOCH_2C$≡CH | nD 1.5945(22.8° C.) |
| 67 | $CH_3$ | — | C(Ph)=$NOCH_2C$≡CBr | |
| 68 | $CH_3$ | — | C(Ph)=$NOCH_2C$≡CCl | |
| 69 | $CH_3$ | — | C(Ph)=$NOCH_2Ph$ | nD 1.6183(23.9° C.) |

TABLE 1-continued

General formula (I)

$$\text{(I)}$$

| No | R$^1$ | A | B | Property |
|---|---|---|---|---|
| 70 | CH$_3$ | — | C(Ph)=NOCH$_2$(4-Cl-Ph) | |
| 71 | CH$_3$ | — | C(Ph)=NOCH$_2$(3,4-Cl$_2$-Ph) | |
| 72 | CH$_3$ | — | C(Ph)=NOCH$_2$(2,4,6-Cl$_3$-Ph) | |
| 73 | CH$_3$ | — | C(Ph)=NOCH$_2$(2-CH$_3$-Ph) | |
| 74 | CH$_3$ | — | C(Ph)=NOCH$_2$(3-CH$_3$-Ph) | |
| 75 | CH$_3$ | — | C(Ph)=NOCH$_2$(4-CH$_3$-Ph) | |
| 76 | CH$_3$ | — | C(Ph)=NOCH$_2$(3-CH$_3$O-Ph) | |
| 77 | CH$_3$ | — | C(=N$^+$CH$_3$)—Ph ↓ O$^-$ | m. p. 180.1° C. |
| 78 | CH$_3$ | — | C(=N$^+$CH$_2$Ph)Ph ↓ O$^-$ | m. p. 116.3° C. |
| 79 | CH$_3$ | — | C(Ph)=NNH$_2$ | m. p. 72.3° C. |
| 80 | CH$_3$ | — | C(Ph)=NNHCOCC$_2$H$_5$ | |
| 81 | CH$_3$ | — | C(Ph)=NNHCSNHPh | |
| 82 | CH$_3$ | — | 3-CN—Q$_2$ | m. p. 190–200° C. |
| 83 | CH$_3$ | — | Q$_4$ | |
| 84 | CH$_3$ | — | 5-CH$_3$-5-i-C$_3$H$_7$-4-(=O)—Q$_4$ | m. p. 59° C. |
| 85 | CH$_3$ | — | 5-(CH$_3$)$_2$—Q$_5$ | m. p. 114° C. |
| 86 | CH$_3$ | — | 4-(CH$_3$)$_2$-5-(=O)—Q$_6$ | m. p. 107° C. |
| 87 | CH$_3$ | — | 4,6-(CH$_3$)$_2$—Q$_3$ | m. p. >180° C. |
| 88 | CH$_3$ | — | 4-CH$_3$—Q$_7$ | m. p. 89° C. |
| 89 | CH$_3$ | — | 4-t-C$_4$H$_5$—Q$_7$ | m. p. 61° C. |
| 90 | CH$_3$ | — | 4-(2-Cl-Ph)-Q$_7$ | m. p. 136° C. |
| 91 | CH$_3$ | — | 4-(4-Cl-Ph)-Q$_7$ | m. p. 125° C. |
| 92 | CH$_3$ | — | 4-(2,4-C$_{12}$-Ph)-Q$_7$ | m. p. 170° C. |
| 93 | CH$_3$ | — | 4-(4-CH$_3$-Ph)-Q$_7$ | m. p. 118° C. |
| 94 | CH$_3$ | — | 5-CH$_3$-4-Ph-Q$_7$ | m. p. 151° C. |
| 95 | CH$_3$ | — | 4-CONHCH$_3$—Q$_7$ | m. p. 144° C. |
| 96 | CH$_3$ | — | 4-CH$_2$COOH—Q | m. p. 196° C. |
| 97 | CH$_3$ | — | 4-CH$_2$CONH$_2$—Q$_7$ | m. p. 182° C. |
| 98 | CH$_3$ | — | 4-CH$_2$COOC$_2$H$_5$—Q$_7$ | m. p. 98° C. |
| 99 | CH$_3$ | — | 4-CH$_2$CONHCH$_3$—Q$_7$ | m. p. 155° C. |
| 100 | CH$_3$ | — | 4-CH$_2$CON(C$_2$H$_5$)$_2$—Q$_7$ | m. p. 132° C. |
| 101 | CH$_3$ | — | 5-Ph-Q$_8$ | m. p. 154° C. |
| 102 | CH$_3$ | — | 5-SH—Q$_8$ | m. p. 182° C. |
| 103 | CH$_3$ | — | 5-SCH$_3$—Q$_8$ | m. p. 65° C. |
| 104 | CH$_3$ | CH$_2$ | Cl | nD 1.5590(26° C.) |
| 105 | CH$_3$ | CH$_2$ | OH | nD 1.553(21° C.) |
| 106 | CH$_3$ | CH$_2$ | OCH$_3$ | nD 1.5180(26° C.) |
| 107 | CH$_3$ | CH$_2$ | OC$_4$H$_9$-n | |
| 108 | CH$_3$ | CH$_2$ | OC$_8$H$_{17}$-n | |
| 109 | CH$_3$ | CH$_2$ | OCH$_2$Ph | nD 1.5730(25° C.) |
| 110 | CH$_3$ | CH$_2$ | OCH$_2$(2-Cl-Ph) | |
| 111 | CH$_3$ | CH$_2$ | OCH$_2$(3-Cl-Ph) | |
| 112 | CH$_3$ | CH$_2$ | OCH$_2$(4-Cl-Ph) | |
| 113 | CH$_3$ | CH$_2$ | OCH$_2$(2-CH$_3$-Ph) | |
| 114 | CH$_3$ | CH$_2$ | OCH$_2$(3-CH$_3$-Ph) | |
| 115 | CH$_3$ | CH$_2$ | OCH$_2$(4-t-C$_4$H$_9$-Ph) | |
| 116 | CH$_3$ | CH$_2$ | OCH$_2$(4-CF$_3$-Ph) | |
| 117 | CH$_3$ | CH$_2$ | OCH$_2$(2,4-(CH$_3$)$_2$-Ph) | |
| 118 | CH$_3$ | CH$_2$ | OCH$_2$(3,4-(CH$_3$)$_2$-Ph) | |
| 119 | CH$_3$ | CH$_2$ | OCH$_2$(4-OH-Ph) | |
| 120 | CH$_3$ | CH$_2$ | OCH$_2$(4-CH$_3$O-Ph) | |
| 121 | CH$_3$ | CH$_2$ | OCH$_2$(4-CF$_3$O-Ph) | |
| 122 | CH$_3$ | CH$_2$ | OCH$_2$(2,4-(CH$_3$O)$_2$-Ph) | |
| 123 | CH$_3$ | CH$_2$ | OCH$_2$(3,4-(CH$_3$O)$_2$-Ph) | |
| 124 | CH$_3$ | CH$_2$ | OCH$_2$(4-NH$_2$-Ph) | |
| 125 | CH$_3$ | CH$_2$ | OCH$_2$(4-NO$_2$-Ph) | |
| 126 | CH$_3$ | CH$_2$ | OCH$_2$(4-COCCH$_3$-Ph) | |
| 127 | CH$_3$ | CH$_2$ | OCH$_2$(4-COOC$_4$H$_9$-t-Ph) | |
| 128 | CH$_3$ | CH$_2$ | OCH$_2$(4-CN-Ph) | |
| 129 | CH$_3$ | CH$_2$ | OCH$_2$(4-CH$_3$—Q$_1$) | nD 1.547(26.3° C.) |

TABLE 1-continued

General formula (I)

$$\text{(I)}$$

| No | R¹ | A | B | Property |
|---|---|---|---|---|
| 130 | CH₃ | CH₂ | OPh | |
| 131 | CH₃ | CH₂ | O(2-Cl-Ph) | |
| 132 | CH₃ | CH₂ | O(3-Cl-Ph) | |
| 133 | CH₃ | CH₂ | O(4-Cl-Ph) | |
| 134 | CH₃ | CH₂ | O(2-CH₃-Ph) | |
| 135 | CH₃ | CH₂ | O(3-CH₃-Ph) | |
| 136 | CH₃ | CH₂ | O(4-t-C₄H₉-Ph) | |
| 137 | CH₃ | CH₂ | O(4-CF₃-Ph) | |
| 138 | CH₃ | CH₂ | O(2,4-(CH₃)₂-Ph) | |
| 139 | CH₃ | CH₂ | O(3,4-(CH₃)2-Ph) | |
| 140 | CH₃ | CH₂ | O(4-OH-Ph) | |
| 141 | CH₃ | CH₂ | O(4-CH₃O-Ph) | |
| 142 | CH₃ | CH₂ | O(4-CF₃O-Ph) | |
| 143 | CH₃ | CH₂ | O(2,4-(CH₃O)₂-Ph) | |
| 144 | CH₃ | CH₂ | O(3,4-(CH₃O)₂-Ph) | |
| 145 | CH₃ | CH₂ | O(4-NH₂-Ph) | |
| 146 | CH₃ | CH₂ | O(4-NO₂-Ph) | |
| 147 | CH₃ | CH₂ | O(4-COOCH₃-Ph) | |
| 148 | CH₃ | CH₂ | O(4-COOC₄H₉-t-Ph) | |
| 149 | CH₃ | CH₂ | O(4-CN-Ph) | |
| 150 | CH₃ | CH₂ | O—COCH₃ | nD 1.3580(25° C.) |
| 151 | CH₃ | CH₂ | O—COC₂H₅ | |
| 152 | CH₃ | CH₂ | O—COC₃H₇-n | |
| 153 | CH₃ | CH₂ | O—COC₃H₇-i | |
| 154 | CH₃ | CH₂ | O—COC₄H₉-t | |
| 155 | CH₃ | CH₂ | O—COC₄H₉-s | |
| 156 | CH₃ | CH₂ | O—COCl₇H₃₅-n | |
| 157 | CH₃ | CH₂ | O—COC₆H₁₁-cyclo | |
| 158 | CH₃ | CH₂ | O—COCH=CH₂ | |
| 159 | CH₃ | CH₂ | O—COCH=CHPh | |
| 160 | CH₃ | CH₂ | O—COCH₂Cl | |
| 161 | CH₃ | CH₂ | O—COCF₃ | |
| 162 | CH₃ | CH₂ | O—COPh | m. p. 50–53° C. |
| 163 | CH₃ | CH₂ | O—CO(2-Cl-Ph) | |
| 164 | CH₃ | CH₂ | O—CO(3-Cl-Ph) | |
| 165 | CH₃ | CH₂ | O—CO(4-Cl-Ph) | |
| 166 | CH₃ | CH₂ | O—CO(2-CH₃-Ph) | |
| 167 | CH₃ | CH₂ | O—CO(3-CH₃-Ph) | |
| 168 | CH₃ | CH₂ | O—CO(4-t-C₄H₉-Ph) | |
| 169 | CH₃ | CH₂ | O—CO(4-CF₃-Ph) | |
| 170 | CH₃ | CH₂ | O—CO(2,4-(CH₃)₂-Ph) | |
| 171 | CH₃ | CH₂ | O—CO(3,4-(CH₃)₂-Ph) | |
| 172 | CH₃ | CH₂ | O—CO(4-CH₃O-Ph) | |
| 173 | CH₃ | CH₂ | O—CO(4-CF₃O-Ph) | |
| 174 | CH₃ | CH₂ | O—CO(2,4-(CH₃O)₂-Ph) | |
| 175 | CH₃ | CH₂ | O—CO(3,4-(CH₃O)₂-Ph) | |
| 176 | CH₃ | CH₂ | O—CO(4-NO₂-Ph) | |
| 177 | CH₃ | CH₂ | O—CO(4-CCOCH₃-Ph) | |
| 178 | CH₃ | CH₂ | O—CO(4-CCOC₄H₉-t-Ph) | |
| 179 | CH₃ | CH₂ | O—CO(4-CN-Ph) | |
| 180 | CH₃ | CH₂ | O—COOC₂H₅ | nD 1.5041(26° C.) |
| 181 | CH₃ | CH₂ | O—COOC₄H₉-i | |
| 182 | CH₃ | CH₂ | ON=C(CH₃)₂ | |
| 183 | CH₃ | CH₂ | ON=C(CH₃)C₂H₅ | |
| 184 | CH₃ | CH₂ | ON=C₆H₁₀-cyclo | |
| 185 | CH₃ | CH₂ | ON=CHPh | |
| 186 | CH₃ | CH₂ | ON=CH(2-Cl-Ph) | |
| 187 | CH₃ | CH₂ | ON=CH(3-Cl-Ph) | |
| 188 | CH₃ | CH₂ | ON=CH(4-Cl-Ph) | |
| 189 | CH₃ | CH₂ | ON=CH(2-CH₃-Ph) | |
| 190 | CH₃ | CH₂ | ON=CH(3-CH₃-Ph) | |
| 191 | CH₃ | CH₂ | ON=CH(4-C₄H₉-t-Ph) | |
| 192 | CH₃ | CH₂ | ON=CH(4-CF₃-Ph) | |
| 193 | CH₃ | CH₂ | ON=CH(2,4-(CH₃)₂-Ph) | |
| 194 | CH₃ | CH₂ | ON=CH(3,4-(CH₃)₂-Ph) | |
| 195 | CH₃ | CH₂ | ON=CH(4-CH-Ph) | |
| 196 | CH₃ | CH₂ | ON=CH(4-CH₃C-Ph) | |
| 197 | CH₃ | CH₂ | ON=CH(4-CF₃C-Ph) | |

TABLE 1-continued

General formula (I)

$$\text{(I)}$$

| No | R¹ | A | B | Property |
|---|---|---|---|---|
| 198 | CH₃ | CH₂ | ON=CH(2,4-(CH₃C)₂-Ph) | |
| 199 | CH₃ | CH₂ | ON=CH(3,4-(CH₃C)₂-Ph) | |
| 200 | CH₃ | CH₂ | ON=CH(4-NH₂-Ph) | |
| 201 | CH₃ | CH₂ | ON=CH(4-NC₂-Ph) | |
| 202 | CH₃ | CH₂ | ON=CH(4-COOCH₃-Ph) | |
| 203 | CH₃ | CH₂ | ON=C(CH₃)Ph | |
| 204 | CH₃ | CH₂ | OSO₂CH₃ | |
| 205 | CH₃ | CH₂ | OSO₂CF₃ | |
| 206 | CH₃ | CH₂ | OSO₂Ph | |
| 207 | CH₃ | CH₂ | OSO₂(4-Br-Ph) | |
| 208 | CH₃ | CH₂ | OSO₂(4-CH₃-Ph) | Paste |
| 209 | CH₃ | CH₂ | SPh | nD 1.636(24.6° C.) |
| 210 | CH₃ | CH₂ | SOPh | |
| 211 | CH₃ | CH₂ | SO₂Ph | m. p. 118° C. |
| 212 | CH₃ | CH₂ | SO₂(4-CH₃-Ph) | |
| 213 | CH₃ | CH₂ | SO₂(4-NO₂-Ph) | |
| 214 | CH₃ | CH₂ | SCH₂Ph | nD 1.612(24.6° C.) |
| 215 | CH₃ | CH₂ | SO₂CH₂Ph | m. p. 116° C. |
| 216 | CH₃ | CH₂ | SCON(CH₂CH=CH₂)₂ | |
| 217 | CH₃ | CH₂ | SCO—Q₉ | |
| 218 | CH₃ | CH₂ | SCOOC₂H₅ | |
| 219 | CH₃ | CH₂ | SCSN(C₂H₅)₂ | |
| 220 | CH₃ | CH₂ | NH₂.HCl | m. p. >250° C. |
| 221 | CH₃ | CH₂ | N(C₂H₅)₂ | Paste |
| 222 | CH₃ | CH₂ | N(CH₂CH=CH₂)₂ | Paste |
| 223 | CH₃ | CH₂ | NHPh | |
| 224 | CH₃ | CH₂ | NH(4-CH₃-Ph) | |
| 225 | CH₃ | CH₂ | NHCOCH₃ | |
| 226 | CH₃ | CH₂ | NHCOC₂H₅ | |
| 227 | CH₃ | CH₂ | NHCOC₃H₇-n | |
| 228 | CH₃ | CH₂ | NHCOC₃H-i | |
| 229 | CH₃ | CH₂ | NHCOC₄H₉-t | m. p. 93–94° C. |
| 230 | CH₃ | CH₂ | NHCOC₄H₉-s | |
| 231 | CH₃ | CH₂ | NHCOC₁₇H₃₅-n | |
| 232 | CH₃ | CH₂ | NHCOC₃H₅-cyclo | m. p. 75–78° C. |
| 233 | CH₃ | CH₂ | NHCO(2,2-Cl₂—C₃H₅-cyclo) | |
| 234 | CH₃ | CH₂ | NHCOC₆H₁₁-cyclo | |
| 235 | CH₃ | CH₂ | NHCOCH=CH₂ | |
| 236 | CH₃ | CH₂ | NHCOCH=CHPh | |
| 237 | CH₃ | CH₂ | NHCOCH₂Cl | |
| 238 | CH₃ | CH₂ | NHCOCF₃ | |
| 239 | CH₃ | CH₂ | NHCOPh | m. p. 96° C. |
| 240 | CH₃ | CH₂ | NHCO(2-Cl-Ph) | |
| 241 | CH₃ | CH₂ | NHCO(3-Cl-Ph) | |
| 242 | CH₃ | CH₂ | NHCO(4-Cl-Ph) | |
| 243 | CH₃ | CH₂ | NHCO(2-CH₃-Ph) | |
| 244 | CH₃ | CH₂ | NHCO(3-CH₃-Ph) | |
| 245 | CH₃ | CH₂ | NHCO(4-t-C₄H₉-Ph) | |
| 246 | CH₃ | CH₂ | NHCO(3-CF₃-Ph) | |
| 247 | CH₃ | CH₂ | NHCO(4-CF₃-Ph) | |
| 248 | CH₃ | CH₂ | NHCO(2,4-(CH₃)₂-Ph) | |
| 249 | CH₃ | CH₂ | NHCO(3,4-(CH₃)₂-Ph) | |
| 250 | CH₃ | CH₂ | NHCO(4-OH-Ph) | |
| 251 | CH₃ | CH₂ | NHCO(4-CH₃O-Ph) | |
| 252 | CH₃ | CH₂ | NHCO(4-CF₃O-Ph) | |
| 253 | CH₃ | CH₂ | NHCO(2,4-(CH₃O)₂-Ph) | |
| 254 | CH₃ | CH₂ | NHCO(3,4-(CH₃O)₂-Ph) | |
| 255 | CH₃ | CH₂ | NHCO(4-NH₂-Ph) | |
| 256 | CH₃ | CH₂ | NHCO(4-NO₂-Ph) | |
| 257 | CH₃ | CH₂ | NHCO(4-COOCH₃-Ph) | |
| 258 | CH₃ | CH₂ | NHCO(2,4-Cl₂-Ph) | |
| 259 | CH₃ | CH₂ | NHCO(3,4-Cl₂-Ph) | |
| 260 | CH₃ | CH₂ | N(CHO)₂ | m. p. 70–75° C. |
| 261 | CH₃ | CH₂ | Q₁₀ | |
| 262 | CH₃ | CH₂ | 3,3,4,4,5,5-F₆—Q₁₁ | |
| 263 | CH₃ | CH₂ | Q₁₂ | m. p. 124–125° C. |
| 264 | CH₃ | CH₂ | NHCOOCH₃ | |
| 265 | CH₃ | CH₂ | NHCOOC₂H₅ | Paste |

TABLE 1-continued

General formula (I)

$$\text{(I)}$$

| No | R$^1$ | A | B | Property |
|---|---|---|---|---|
| 266 | CH$_3$ | CH$_2$ | NHCOOC$_4$H$_9$-i | |
| 267 | CH$_3$ | CH$_2$ | NHCOOC$_4$H$_9$-t | |
| 268 | CH$_3$ | CH$_2$ | NHCOO(4-NO$_2$-Ph) | |
| 269 | CH$_3$ | CH$_2$ | NHCOOPh | |
| 270 | CH$_3$ | CH$_2$ | NHCONHCH$_3$ | |
| 271 | CH$_3$ | CH$_2$ | NHCONHC$_2$H$_5$ | |
| 272 | CH$_3$ | CH$_2$ | NHCONHC$_3$H$_7$-i | |
| 273 | CH$_3$ | CH$_2$ | NHCONHPh | m. p. 145° C. |
| 274 | CH$_3$ | CH$_2$ | NHCONH(2-Cl-Ph) | |
| 275 | CH$_3$ | CH$_2$ | NHCONH(3-Cl-Ph) | |
| 276 | CH$_3$ | CH$_2$ | NHCONH(4-Cl-Ph) | |
| 277 | CH$_3$ | CH$_2$ | NHCONH(2-CH$_3$-Ph) | |
| 278 | CH$_3$ | CH$_2$ | NHCONH(3-CH$_3$-Ph) | |
| 279 | CH$_3$ | CH$_2$ | NHCONH(4-t-C$_4$Hg-Ph) | |
| 280 | CH$_3$ | CH$_2$ | NHCONH(3-CF$_3$-Ph) | |
| 281 | CH$_3$ | CH$_2$ | NHCONH(4-CF$_3$-Ph) | |
| 282 | CH$_3$ | CH$_2$ | NHCONH(2,4-(CH$_3$)$_2$-Ph) | |
| 283 | CH$_3$ | CH$_2$ | NHCONH(3,4-(CH$_3$)$_2$-Ph) | |
| 284 | CH$_3$ | CH$_2$ | NHCONH(4-OH-Ph) | |
| 285 | CH$_3$ | CH$_2$ | NHCONH(3-CH$_3$O-Ph) | |
| 286 | CH$_3$ | CH$_2$ | NHCONH(4-i-C$_3$H$_7$O-Ph) | |
| 287 | CH$_3$ | CH$_2$ | NHCONH(4-CF$_3$O-Ph) | |
| 288 | CH$_3$ | CH$_2$ | NHCONH(2,4-(CH$_3$O)$_2$-Ph) | |
| 289 | CH$_3$ | CH$_2$ | NHCONH(3,4-(CH$_3$O)2-Ph) | |
| 290 | CH$_3$ | CH$_2$ | NHCONH(4-NH$_2$-Ph) | |
| 291 | CH$_3$ | CH$_2$ | NHCONH(4-NO$_2$-Ph) | |
| 292 | CH$_3$ | CH$_2$ | NHCONH(4-COOCH$_3$-Ph) | |
| 293 | CH$_3$ | CH$_2$ | NHCONH(2,4-C$_{12}$-Ph) | |
| 294 | CH$_3$ | CH$_2$ | NHCSNHCH$_3$ | |
| 295 | CH$_3$ | CH$_2$ | NHCSNHPh | m. p. 171–172° C. |
| 296 | CH$_3$ | CH$_2$ | NHC(=NCH$_3$)OC$_2$H$_5$ | |
| 297 | CH$_3$ | CH$_2$ | NHC(=NPh)N(C$_2$H$_5$)$_2$ | |
| 298 | CH$_3$ | CH$_2$ | NHC(=NPh)SCH$_3$ | |
| 299 | CH$_3$ | CH$_2$ | NHSO$_2$(4-CH$_3$-Ph) | Paste |
| 300 | CH$_3$ | CH$_2$ | NHNH$_2$ | |
| 301 | CH$_3$ | CH$_2$ | NHN=C(CH$_3$)$_2$ | |
| 302 | CH$_3$ | CH$_2$ | NHN=CHPh | |
| 303 | CH$_3$ | CH$_2$ | NHN=C(CH$_3$)ph | |
| 304 | CH$_3$ | CH$_2$ | Q$_3$ | |
| 305 | CH$_3$ | CH$_2$ | Q$_{14}$ | |
| 306 | CH$_3$ | CH$_2$ | Q$_{16}$ | |
| 307 | CH$_3$ | CH$_2$ | CHO | |
| 308 | CH$_3$ | CH$_2$ | CN | |
| 309 | CH$_3$ | CH$_2$ | COOCH$_3$ | |
| 310 | CH$_3$ | CH$_2$ | COOC$_2$H$_5$ | |
| 311 | CH$_3$ | CH$_2$ | COOC$_3$H$_7$-i | |
| 312 | CH$_3$ | CH$_2$ | COOC$_8$H$_{17}$-n | |
| 313 | CH$_3$ | CH$_2$ | COOCH$_2$CH=CH$_2$ | |
| 314 | CH$_3$ | CH$_2$ | CONH$_2$ | |
| 315 | CH$_3$ | CH$_2$ | CONHCH$_3$ | |
| 316 | CH$_3$ | CH$_2$ | CONHC$_3$H$_7$-i | |
| 317 | CH$_3$ | CH$_2$ | CON(CH$_3$)$_2$ | |
| 318 | CH$_3$ | CH$_2$ | CO—Q$_{16}$ | |
| 319 | CH$_3$ | CH$_2$ | CO—Q$_{17}$ | |
| 320 | CH$_3$ | CH$_2$ | CO—Q$_{18}$ | |
| 321 | CH$_3$ | CH$_2$ | CO—Q$_{19}$ | |
| 322 | CH$_3$ | CH$_2$ | CH(CCCH$_3$)$_2$ | |
| 323 | CH$_3$ | CH$_2$ | CH(COOC$_2$H$_5$)$_2$ | |
| 324 | CH$_3$ | CH$_2$ | C(NHCOCH$_3$)(COCC$_2$H$_5$)$_2$ | m. p. 93–97° C. |
| 325 | CH$_3$ | CH$_2$ | CH(SCH$_3$)(SOCH$_3$) | |
| 326 | CH$_3$ | CH$_2$ | Q$_{20}$ | |
| 327 | CH$_3$ | CHCl | COOCH$_3$ | nD 1. 5456(23° C.) |
| 328 | CH$_3$ | CHCH$_3$ | CN | |
| 329 | CH$_3$ | CHCH$_3$ | COOCH$_3$ | |
| 330 | CH$_3$ | C(CH$_3$)$_2$ | CN | |
| 331 | CR$_3$ | C(CH$_3$)$_2$ | COOCH$_3$ | |
| 332 | CH$_3$ | CHPh | Cl | nD 1.5979(21.8° C.) |
| 333 | CH$_3$ | CHPh | OH | m. p. 93.2° C. |

TABLE 1-continued

General formula (I)

$$\text{(I)}$$

| No | R$^1$ | A | B | Property |
|---|---|---|---|---|
| 334 | CH$_3$ | CHPh | OCH$_3$ | |
| 335 | CH$_3$ | CHPh | CN | |
| 336 | CH$_3$ | CHPh | COOH | |
| 337 | CH$_3$ | CH$_2$CH$_2$ | COOCH$_3$ | |
| 338 | CH$_3$ | CH=CH (E) | COOCH$_3$ | m. p. 70° C. |
| 339 | CH$_3$ | CH=CH (E) | CON(CH$_3$)$_2$ | |
| 340 | CH$_3$ | CH=CH (E) | CONHPh | |
| 341 | CH$_3$ | CH=CH (Z) | COOCH$_3$ | m. p. 80–85° C. |
| 342 | CH$_3$ | CH=CH (E, Z mixture) | CHO | m. p. 77–78° C. |
| 343 | CH$_3$ | C=C(SCH$_3$)$_2$ | CN | |
| 344 | CH$_3$ | Q$_{21}$ | CN | |
| 345 | CH$_3$ | C=C(COOCH$_3$)$_2$ | H | |
| 346 | CH$_3$ | C=C(COOCH$_3$)CN | H | Paste |
| 347 | CH$_3$ | Q$_{22}$ | CN | |
| 348 | C$_2$H$_5$ | CH$_2$ | Cl | |
| 349 | C$_2$H$_5$ | CH$_2$ | OH | |
| 350 | C$_2$H$_5$ | CH$_2$ | OCH$_3$ | |
| 351 | C$_2$H$_5$ | CH$_2$ | OCH$_2$Ph | |
| 352 | C$_2$H$_5$ | CH$_2$ | OCH$_2$(4-C$_2$H$_5$—Q$_1$) | |
| 353 | C$_3$H$_7$-i | CH$_2$ | F | |
| 354 | C$_3$H$_7$-i | CH$_2$ | Cl | |
| 355 | C$_3$H$_7$-i | CH$_2$ | Br | |
| 356 | C$_3$H$_7$-i | CH$_2$ | I | |
| 357 | C$_3$H$_7$-i | CH$_2$ | OH | |
| 358 | C$_3$H$_7$-i | CH$_2$ | OCH$_3$ | |
| 359 | C$_3$H$_7$-i | CH$_2$ | OCH$_2$Ph | |
| 360 | C$_3$H$_7$-i | CH$_2$ | OCH$_2$(4-i-C$_3$H$_7$—Q$_1$) | |
| 361 | C$_3$H$_7$-i | CH$_2$ | NH$_2$.HCl | |
| 362 | C$_3$H$_7$-i | CH$_2$ | N(CH$_3$)$_2$ | |
| 363 | C$_3$H$_7$-i | CH$_2$ | N(CH$_2$CH=CH$_2$)$_2$ | |
| 364 | C$_3$H$_7$-i | CH$_2$ | NHCOCH$_3$ | |
| 365 | CH$_2$Cl | CH$_2$ | OH | Paste |
| 366 | CF$_3$ | CH$_2$ | OH | |
| 367 | Ph | — | Q$_4$ | m. p. 150° C. |
| 368 | Ph | — | Q$_5$ | m. p. 158° C. |
| 369 | Ph | — | 5-(CH$_3$)$_2$—Q$_5$ | m. p. 147° C. |
| 370 | Ph | — | 4-CH$_3$—Q$_7$ | m. p. 161° C. |
| 371 | Ph | — | 4-t-C$_4$H$_9$—Q$_7$ | m. p. 110° C. |
| 372 | Ph | — | 4-COOCH$_3$—Q$_7$ | m. p. 124° C. |
| 373 | Ph | — | 4-CONHCH$_3$—Q$_7$ | m. p. 187° C. |
| 374 | Ph | — | 4-CH$_2$COOH—Q$_7$ | m. p. 137° C. |
| 375 | Ph | — | 4-CH$_2$CONH$_2$—Q$_7$ | m. p. 137° C. |
| 376 | Ph | — | 4-CH$_2$CONHCH$_3$—Q$_7$ | m. p. 154° C. |
| 377 | Ph | — | 5-CH$_3$—Q$_{23}$ | m. p. 85° C. |
| 378 | Ph | CH$_2$ | Cl | |
| 379 | Ph | CH$_2$ | OH | |
| 380 | Ph | CH$_2$ | OCH$_3$ | |
| 381 | Ph | CH$_2$ | OCH$_2$Ph | |
| 382 | Ph | CH$_2$ | OCH$_2$(4-Ph—Q$_1$) | |
| 383 | Ph | CH$_2$ | COOCH$_3$ | |
| 384 | Ph | CH$_2$ | CON(CH$_3$)Ph | |
| 385 | Ph | CH$_2$ | CONH(4-CH$_3$O-Ph) | m. p. 129° C. |
| 386 | 2-Cl-Ph | CH$_2$ | OH | |
| 387 | 3-Cl-Ph | CH$_2$ | OH | |
| 388 | 4-Cl-Ph | CH$_2$ | OH | |
| 389 | 4-CH$_3$-Ph | CH$_2$ | OH | |
| 390 | 3-CH$_3$-Ph | CH$_2$ | OH | |
| 391 | 4-CH$_3$-Ph | CH$_2$ | OH | |
| 392 | 4-t-C$_4$H$_9$-Ph | CH$_2$ | OH | |
| 393 | 2-CF$_3$-Ph | CH$_2$ | OH | |
| 394 | 4-CF$_3$-Ph | CH$_2$ | OH | |
| 395 | 2,4-(CH$_3$)$_2$-Ph | CH$_2$ | OH | |
| 396 | 3,4-(CH$_3$)$_2$-Ph | CH$_2$ | OH | |
| 397 | 4-OH-Ph | CH$_2$ | OH | |
| 398 | 4-CH$_3$O-Ph | CH$_2$ | OH | |
| 399 | 4-CF$_3$O-Ph | CH$_2$ | OH | |
| 400 | 4-PhO-Ph | CH$_2$ | OH | |

TABLE 1-continued

General formula (I)

$$\begin{array}{c} N{=}{=}{=}R^1 \\ \| \phantom{xxxx} | \\ N \phantom{xx} A{-}B \\ \diagdown_S\diagup \end{array}$$

| No | R$^1$ | A | B | Property |
|---|---|---|---|---|
| 401 | 2,4-(CH$_3$O)$_2$-Ph | CH$_2$ | OH | |
| 402 | 3,4-(CH$_3$O)$_2$-Ph | CH$_2$ | OH | |
| 403 | 4-COOCH$_3$-Ph | CH$_2$ | OH | |
| 404 | 2,4-Cl$_2$-Ph | CH$_2$ | OH | |
| 405 | 3,4-Cl$_2$-Ph | CH$_2$ | OH | |
| 406 | Q$_{24}$ | CH$_2$ | OH | |
| 407 | Q$_{25}$ | CH$_2$ | OH | |
| 408 | Q$_{26}$ | CH$_2$ | OH | |
| 409 | Q$_{27}$ | CH$_2$ | OH | m. p. 158° C. |
| 410 | Q$_{28}$ | CH$_2$ | OH | |
| 411 | 6-Cl—Q$_{27}$ | CH$_2$ | OH | |
| 412 | Q$_{27}$ | — | CN | m. p. 129° C. |
| 413 | 4-F-Ph | CH$_2$ | O—CO-(4-Cl-Ph) | m. p. 79° C. |
| 414 | 4-F-Ph | CH$_2$ | O-(4-CH$_3$O-Ph) | m. p. 86° C. |
| 415 | 4-F-Ph | CH$_2$ | O—CO—CH$_2$-(4-CH$_3$-Ph) | m. p. 113° C. |
| 416 | 4-F-Ph | CH$_2$ | O—CO—NH-Ph | m. p. 99° C. |
| 417 | 4-F-Ph | CH$_2$ | ON=C(CH$_3$)(4-Cl-Ph) | m. p. 91° C. |
| 418 | 4-F-Ph | CH$_2$ | OH | m. p. 100° C. |
| 419 | 4-F-Ph | CH$_2$ | Br | m. p. 88° C. |
| 420 | 4-F-Ph | CH$_2$ | O—CO—CH$_3$ | m. p. 59° C. |
| 421 | Q$_{26}$ | — | CN | m. p. 190° C. |
| 422 | Ph | CH$_2$ | CONH-(4-CH$_3$O-Ph) | m. p. 129° C. |
| 423 | Ph | — | C=NOH(NH$_2$) | m. p. 130° C. |
| 424 | Ph | — | CN | |
| 425 | CH$_3$ | — | Q$_8$ | Paste |
| 426 | CH$_3$ | — | 5-CH$_3$—Q$_8$ | nD 1.5661(26.4° C.) |
| 427 | CH$_3$ | — | SCH$_2$CH=CH$_2$ | Paste |
| 428 | CH$_3$ | — | SCH$_2$C≡CH | Paste |
| 429 | CH$_3$ | — | SCH$_2$-Ph | m. p. 89° C. |
| 430 | CH$_3$ | — | SCH$_2$-(4-t-C$_4$H$_9$-Ph) | m. p. 79° C. |
| 431 | CH$_3$ | — | S—C$_3$H$_7$-i | Paste |
| 432 | CH$_3$ | — | S—CH$_2$—Q$_{27}$ | m. p. 78° C. |
| 433 | CH$_3$ | — | S—CH$_2$—Q$_{23}$ | m. p. 97° C. |

In some of the compounds shown in Table 1, property is expressed by a term of "Paste". Table 2 summarizes the data concerning these compounds.

TABLE 2

| No | H-NMR[CDCl$_3$/TMS, δ value (ppm)] |
|---|---|
| 208 | 2.46(s,3H), 2.63(s,3H), 5.35(s,2H), 7.35(d,2H), 7.77(d,2H). |
| 221 | 1.05(t,6H), 2.54(q,4H), 2.63(s,3H), 3.78(s,2H). |
| 222 | 2.61(s,3H), 3.10–3.12(m,4H), 3.80(s,2H), 5.16–5.24(m,4H), 5.78–5.89(m,2H). |
| 265 | 1.25(t,3H), 2.63(s,3H), 4.15(q,2H), 4.59(d,2H), 5.2–5.35(br,1H). |
| 299 | 2.44(s,3H), 2.58(s,3H), 4.42(d,2H), 5.37(br,t,1H), 7.31(d,2H), 7.70(d,2H). |
| 346 | 1.41(t,3H), 2.90(s,3H), 4.20(q,2H), 8.34(s,1H). |
| 365 | 2.58(t,1H), 5.03(s,2H), 5.16(d,2H). |
| 426 | 3.08(s,3H), 3.96(d,2H), 5.27(d,1H), 5.43(d,1H), 6.00(m,1H). |
| 427 | 3.08(s,3H), 5.23(d,2H), 6.28(s,1H). |
| 430 | 1.55(d,6H), 3.08(s,3H), 4.02(m,1H). |

The 1,2,3-thiadiazole derivatives of the general formula (I) or salts thereof according to the present invention are useful for agricultural and horticultural disease control. For example, these compounds have a very high controlling effect against various diseases, for instance, rice blast (*Pyricularia oryzae*), rice sheath blight (*Rhizoctonia solani*), rice helminthosporium leaf spot (*Cochiobolus miyabeanus*), powdery mildew of various host plants such as powdery mildew of barley and wheat (*Erysiphe graminis*), oats crown rust (*Puccinia coronata*) and rust of other plants, tomato late blight (*Phytophthora infestans*) and late blight or Phytophthora rots of other plants, downy mildew of various plants such as cucumber downy mildew (*Pseudoperonospora cubensis*) and grape downy mildew (*Plasmopara viticola*), apple scab (*Venturia inaequalis*), apple alternaria leaf spot (*AlternariA mali*), pear black spot (*Alternaria kikuchiana*), citrus melanose (*Diaporthe citri*), bacterial diseases including Pseudomonas diseases such as cucumber bacterial blight (*Pseudomonas syrinaae* pv. *lachrymans*) and tomato bacterial wilt (*Pseudomonas solanacearum*), Xanthomonas diseases such as cabbage black rot (*Xanthomonas campestris*), rice bacterial leaf blight (*Xanthomonas oryzae*) and citrus canker (*Xanthomonas citri*) and Erwinia diseases such as cabbage bacterial soft rot (*Erwinia carotovora*), and viral diseases such as tobacco mosaic (*Tobacco mosaic virus*).

The agrohorticultural disease controller containing the 1,2,3-thiadiazole derivative of general formula (I) or salts thereof as an active ingredient according to the present invention exhibits a marked controlling effect against the above-exemplified diseases which damage paddy field crops, upland field crops, fruit trees, vegetables, other crop plants, flowers, ornamental plants, and the like. Accordingly, the desired effects of the agrohorticultural disease controller of the present invention can be exhibited by applying the disease controller to the paddy field water, stalks and leaves or soil of the paddy field, upland field, fruit trees, vegetables, other crops, flowers and ornamental plants at a season at which the diseases are expected to occur, either before their occurrence or at the time when their occurrence has been confirmed.

The agrohorticultural disease controller of the present invention is generally put to use after being prepared into a conveniently usable form according to an ordinary manner for preparation of pesticides.

That is, the 1,2,3-thiadiazole derivative represented by the general formula (I) or a salt thereof according to the present invention and, optionally, an adjuvant are blended with an appropriate inert carrier in a proper proportion and dissolved, separated, suspended, mixed, impregnated, adsorbed or stuck, prepared into a suitable preparation form such as suspension, emulsifiable concentrate, soluble concentrate, wettable powder, granule, dust, tablet, etc. and put to use.

The inert carrier used in the present invention may be either solid or liquid. As the material usable as solid carrier, there can be exemplified soybean flour, cereal flour, wood flour, bark flour, saw dust, powdered tobacco stalks, powdered walnut shells, bran, powdered cellulose, extraction residue of vegetables, powdered synthetic polymers of synthetic resins and the like, clays such as kaolin, bentonite, acid clay and the like, talcs such as talc, pyrophyllite and the like, silica materials such as diatomaceous earth, siliceous sand, mica, white carbon (namely, synthetic, high-dispersion silicic acid , also called finely divided hydrated silica or hydrated silicic acid, some of the commercially available products thereof contain calcium silicate as the major component), activated carbon, powdered sulfur, pumice, calcined diatomaceous earth, crushed brick, fly ash, sand, inorganic mineral powders such as calcium carbonate, calcium phosphate and the like, chemical fertilizers such as ammonium sulfate, ammonium phosphate, ammonium nitrate, urea, ammonium chloride and the like, and compost. These carriers may be used alone or as a mixture thereof.

The material constituting the liquid carrier is selected from materials having a dissolving ability in themselves and materials which have no dissolving ability in themselves but can disperse the active ingredient compound by the aid of an adjuvant. The following are typical examples of the liquid carrier material, which can be used either alone or in the form of a mixture: water; alcohols such as methanol, ethanol, isopropanol, butanol, ethylene glycol and the like; ketones such as acetone, methyl ethyl ketone, methyl isobutyl ketone, diisobutyl ketone, cyclohexanone and the like; ethers such as ethyl ether, dioxane, cellosolve, dipropyl ether, tetrahydrofuran and the like; aliphatic hydrocarbons such as kerosene, mineral oils and the like; aromatic hydrocarbons such as benzene, toluene, xylene, solvent naphtha, alkyl-naphthalene and the like; halogenated hydrocarbons such as dichloroethene, chloroform, carbon tetrachloride, chlorobenzene and the like; esters such as ethyl acetate, diisopropyl phthalate, dibutyl phthalate, dioctyl phthalate and the like; amides such as dimethylformamide, diethylformamide, dimethylacetamide and the like; nitriles such as acetonitrile and the like; dimethyl sulfoxide; etc.

As the adjuvant, the following can be referred to as typical ones. These adjuvants are used depending upon purposes, either alone or in combination of two or more in some cases. It is also possible to use no adjuvant at all, in some cases.

A surfactant is used for the purpose of emulsifying, dispersing, solubilizing and/or wetting an active ingredient compound. As the surfactant, there can be exemplified polyoxyethylene alkyl ethers, polyoxyethylene alkylaryl ethers, polyoxyethylene higher fatty acid esters, polyoxyethylene resin acid esters, polyoxyethylene sorbitan monolaurate, polyoxyethylene sorbitan monooleate, alkylarylsulfonates, naphthalene-sulfonic acid condensates, ligninsulfonic acid salts, higher alcohol sulfuric esters, etc.

The following adjuvants can also be used for the purpose of stabilizing, tackifying and/or binding the dispersion of active ingredient compound: casein, gelatin, starch, methyl cellulose, carboxymethyl cellulose, gum arabic, polyvinyl alcohol, turpentine, bran oil, bentonite, ligninsulfonic acid salts and the like.

Further, wax, stearic acid salts, alkyl phosphates and the like may be used as an adjuvant for the purpose of improving flowability of a solid product.

Further, naphthalenesulfonic acid condensates, polycondensed phosphoric acid salts and the like may also be used as a peptizer for dispersible products.

Adjuvants such as silicone oils may also be used as a defoaming agent.

The content of the active ingredient compound may be increased or decreased according to the need. For example, in dusts and granules, the suitable content thereof is from 0.01 to 50% by weight. In emulsifiable concentrates and wettable powders, too, the suitable content thereof is from 0.01 to 50% by weight.

For controlling various diseases, the agrohorticultural disease controller of the present invention itself or its appropriate dilution or suspension in water or the like is applied to a crop on which the diseases are expected to occur or a site where occurrence of the diseases is undesirable, in an amount effective for disease control. For example, for controlling the diseases of paddy rice, said disease controller can be used by a method such as direct application to regular paddy field, application to a rice nursery bed, dressing of seeds for direct sowing to flooded paddy field, seed disinfection, etc. For controlling the diseases of barley, wheat, oat or the like, the disease controller of the present invention is applied to stalks and leaves or used for soil treatment where the disease controller is absorbed from the roots.

The application amount of the agrohorticultural disease controller of the present invention may vary depending on various factors including purpose of application, objective disease, state of plant growth, tendency of prevalence of the disease, weather, environmental conditions, preparation form, method of application, site of application, time of application, etc. The application amount, however, should be properly chosen in the range of from 0.1 g to 10 kg per 10 ares as expressed in terms of amount of active ingredient compound, depending on purposes.

In order to expand the spectrum of controllable diseases and the time period of effective application or to reduce the dosage, it is also possible to use the disease controller of the present invention in the form of a mixture with other agrohorticultural disease controllers.

Next, typical examples, formulation examples and test examples of the 1,2,3-thiadiazole derivatives of general formula (I) or salts thereof according to the present invention are presented below. The present invention is by no means limited by these examples.

EXAMPLE 1

Production of 4-methyl-1,2,3-thiadiazole-5-carbaldehyde (Compound No. 7)

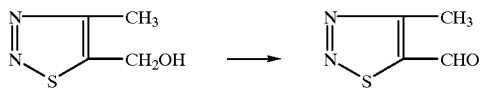

In 25 ml of methylene chloride were suspended 9.9 g (46 mmol) of pyridinium chlorochromate and 10 g of silica gel. After adding 3.0 g (23 mmol) of 4-methyl-1,2,3-thiadiazol-5-ylmethanol, the mixture was stirred at room temperature for 4 hours to make a reaction progress. After the reaction was completed, the reaction mixture was diluted with ether, the resulting florisil was filtered off, the filtrate was concentrated under reduced pressure, and the residue was purified by silica gel column chromatography using 3:1 mixture of n-hexane and ethyl acetate. Thus, 2.0 g of the objective compound was obtained.

Property: nD 1.5555 (26° C.)
Yield: 62%

EXAMPLE 2

Production of 5-benzoyl-4-methyl-1,2,3-thiadiazole (Compound No. 9)

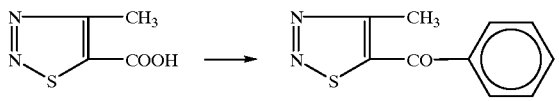

To 2.0 g (15 mimol) of thionyl chloride was added 0.50 g (3.5 mmol) of 4-methyl-1,2,3-thiadiazole-5-carboxylic acid. After heating the mixture with stirring for 2 hours, the thionyl chloride was distilled off under reduced pressure, and the residue was added to a solution of 1.8 g (15 mmol) of aluminum chloride in 20 ml benzene and made to react with heating for 3 hours. After the reaction was completed, the reaction mixture was poured into ice water, the objective product was extracted with ethyl acetate, the organic layer was ashed with a saturated aqueous solution of sodium chloride and dried, the solvent was distilled off under educed pressure, and the residue was purified by silica gel column chromatography using 4:1 mixture of n-hexane and ethyl acetate. Thus, 0.69 g of the objective compound was obtained.

Property: nD 1.6145 (22° C.)
Yield: 97%

EXAMPLE 3

Production of O-benzyl-4-methyl-1,2,3-thiadiazole-5-carbaldehyde oxime (Compound No. 21)

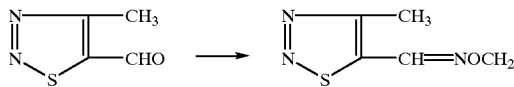

To 10 ml of ethanol were added 0.40 g (3.1 mmol) of 4-methyl-1,2,3-thiadiazole-5-carbaldehyde obtained in Example 1, 0.60 g (3.8 mmol) of benzyloxyamine hydrochloride and 0.50 g (3.8 mmol) of sodium acetate. The mixture was stirred for 4 hours with heating under reflux. After the reaction was completed, the reaction mixture was diluted with ethyl acetate and filtered to remove the precipitate, the filtrate was concentrated under reduced pressure, and the residue was purified by silica gel column chromatography using 4:1 mixture of n-hexane and ethyl acetate. Thus, 0.66 g of the objective compound was obtained.

Property: nD 1.5998 (25° C.)
Yield: 91%

EXAMPLE 4

Production of 5-(5-mercapto-1,3,4-oxadiazol-2-yl)-4-methyl-1,2,3-thiadiazole (Compound No. 102)

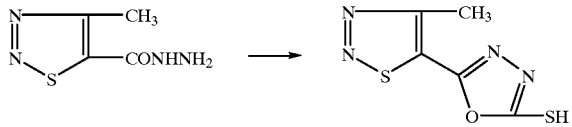

A solution of 0.3 g of potassium hydroxide in 1 ml water and 0.6 ml of carbon disulfide were successively added to a solution of 1.1 g (7.2 mmol) of 4-methyl-1,2,3-thiadiazole-5-carbohydrazide in 15 ml ethanol. The mixture was stirred for 6.5 hours with heating under reflux. After the reaction was completed, the solvent was distilled off under reduced pressure, water was added to the residue, acetic acid was added for the sake of acidification, and the deposited crystalline product was collected by filtration. Thus, 0.82 g of the objective compound was obtained.

Property: m.p. 182° C.
Yield: 59%

EXAMPLE 5

Production of 4-methyl-5-(5-methylthio-1,3,4-oxadiazol-2-yl)-1,2,3-thiadiazole (Compound No. 103)

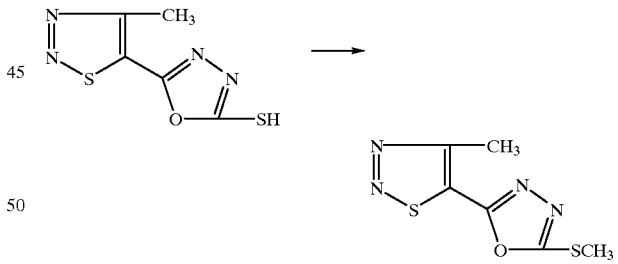

To 10 ml of acetone were added 0.40 g (2.0 mmol) of 5-(5-mercapto-1,3,4-thiadiazol-2-yl)-4-methyl-1,2,3-thiadiazole, 0.43 g (3.0 mmol) of methyl iodide and 0.83 g (6.0 mmol) of potassium carbonate. The mixture was stirred for 5 hours with heating under reflux. After the reaction was completed, the reaction mixture was filtered to remove the insoluble matter, the filtrate was concentrated under reduced pressure, and the residue was purified by silica gel column chromatography using 2:1 mixture of n-hexane and ethyl acetate. Thus, 0.41 g of the objective compound was obtained.

Property: m. p. 65° C.
Yield 96%

EXAMPLE 6

Production of 5-chloromethyl-4-methyl-1,2,3-thiadiazole (Compound No. 104)

While cooling the reaction system with ice, 2 ml of thionyl chloride was added to 0.50 g (3.8 mmol) of 4-methyl-1,2,3-thiadiazol-5-ylmethanol. Then, at room temperature, the mixture was stirred for 2 hours. Then, water was added to stop the reaction, the objective product was extracted with ethyl acetate, the organic layer was washed with water and dried, the solvent was distilled off under reduced pressure, and the residue thus obtained was purified by silica gel column chromatography using 3:1 mixture of n-hexane and ethyl acetate. Thus, 0.46 g of the objective compound was obtained.

Property: nD 1.5590 (26° C.)

Yield: 81%

EXAMPLE 7

Production of 4-methyl-1,2,3-thiadiazol-5-ylmethanol (Compound No. 105)

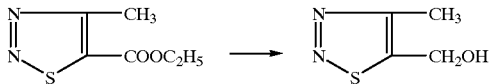

To a solution of 0.10 g (2.5 mmol) of sodium hydroxide in 10 ml ethanol was added 1.0 g (5.8 mmol) of ethyl 4-methyl-1,2,3-thiadiazole-5-carboxylate. Then, 0.33 g (8.7 mmol) of sodium borohydride was added and stirred at room temperature. After the reaction was completed, water was added to the reaction mixture to decompose the excessive sodium borohydride, after which the objective product was extracted with ethyl acetate. The organic layer was washed with water and dried, the solvent was distilled off under reduced pressure, and the residue was purified by silica gel column chromatography using 2:1 mixture of n-hexane and ethyl acetate. Thus, 0.36 g of the objective compound was obtained.

Property: nD 1.553 (21° C.)

Yield: 48%

EXAMPLE 8

Production of 4-methyl-5-benzyloxymethyl-1,2,3-thiadiazole (Compound No. 109)

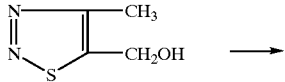

-continued

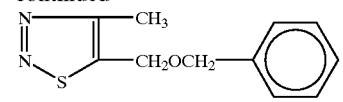

In 10 ml of acetone was dissolved 0.40 g (3.1 mmol) of 4-methyl-1,2,3-thiadiazol-5-ylmethanol. After adding 1.6 g (12 mmol) of potassium carbonate and 0.80 g (4.5 mmol) of benzyl bromide, the resulting mixture was stirred for 10 hours with heating under reflux. After the reaction was completed, the insoluble matter was filtered off, the solvent was distilled off from the filtrate under reduced pressure, and the residue was purified by silica gel column chromatography using 3:1 mixture of n-hexane and ethyl acetate. Thus, 0.65 g of the objective compound was obtained.

Property: nD 1.5730 (25° C.)

Yield 96%

EXAMPLE 9

Production of 4,4'-dimethyl-5,5'-oxybis(methyl-1,2,3-thiadiazole) (Compound No. 129)

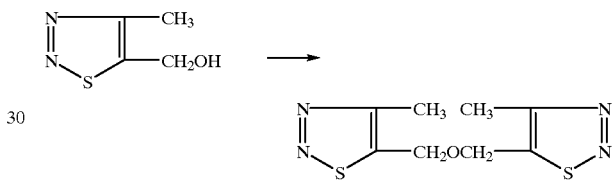

In 20 ml of tetrahydrofuran were dissolved 2.0 g (15 mmol) of 4-methyl-1,2,3-thiadiazol-5-ylmethanol and 3.9 g (39 mmol) of triethylamine. While cooling the system with ice, 3.5 g (18 mmol) of tosyl chloride was added and stirred at room temperature for 24 hours. Then, a saturated aqueous solution of sodium chloride was added to the reaction mixture to stop the reaction, the objective product was extracted with ethyl acetate, the extract solution was washed successively with dilute hydrochloric acid, a saturated aqueous solution of sodium hydrogen carbonate and a saturated aqueous solution of sodium chloride, the solvent was distilled off under reduced pressure, and the residue was purified by silica gel column chromatography using 4:1 mixture of n-hexane and ethyl acetate. Thus, 1.1 g of the objective compound was obtained.

Property: nD 1.547 (26° C.)

Yield: 57%

EXAMPLE 10

Production of 4-methyl-1,2,3-thiadiazol-5-ylmethyl acetate (Compound No.150)

In 10 ml of tetrahydrofuran were dissolved 0.50 g (3.8 mmol) of 4-methyl-1,2,3-thiadiazol-5--ylmethanol, 0.50 g (5.7 numol) of acetyl chloride and 0.80 g (7.6 numol) of triethylamine. The solution thus obtained was stirred at room temperature for 18 hours. Then, a saturated aqueous solution of sodium chloride was added to the reaction mixture to stop the reaction, the objective product was extracted with ethyl acetate, the organic layer was washed with water and dried, the solvent was distilled off under reduced pressure, and the residue was purified by silica gel column chromatography using 3:1 mixture of n-hexane and ethyl acetate. Thus, 0.70 g of the objective compound was obtained.

Property: nD 1.3580 (25° C.)

Yield: 100

EXAMPLE 11

Production of ethyl 4-methyl-1,2,3-thiadiazol-5-ylmethyl carbonate (Compound No. 180)

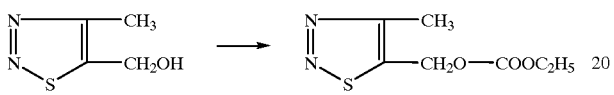

In 5 ml of tetrahydrofuran was dissolved 0.50 g (3.8 mmol) of 4-methyl-1,2,3-thiadiazol-5-ylmethanol. After adding 0.80 g (7.6 mmol) of triethylamine and 0.60 g (5.7 mmol) of ethyl chlorocarbonate, the resulting mixture was stirred at room temperature for 22 hours. Then, water was added to the reaction mixture to stop the reaction, the objective product was extracted with ethyl acetate, the organic layer was washed with water and dried, the solvent was distilled off under reduced pressure, and the residue was purified by silica gel column chromatography using 5:1 mixture of n-hexane and ethyl acetate. Thus, 0.50 g of the objective compound was obtained.

Property: nD 1.5041 (26° C.)

Yield: 68%

EXAMPLE 12

Production of 4-methyl-5-phenylthiomethyl-1,2,3-thiadiazole (Compound No. 209)

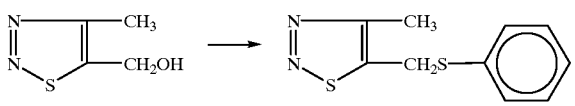

At an ice-cooled temperature, 3 ml of thionyl chloride was added to 0.50 g (3.8 mmol) of 4-methyl-1,2,3-thiadiazol-5-ylmethanol and stirred for 4 hours. Then, the reaction mixture was concentrated under reduced pressure, and 1.30 g (11.5 mmol) of potassium carbonate, 0.38 g (3.4 mmol) of thiophenol and 10 ml of acetone were added to the concentrate and reacted for 7 hours with heating under reflux. After the reaction was completed, the reaction mixture was cooled to room temperature, the precipitated matter was filtered off, the solvent was distilled off under reduced pressure, and the residue was purified by silica gel column chromatography using 5:1 mixture of n-hexane and ethyl acetate. Thus, 0.64 g of the objective compound was obtained.

Property: nD 1.636 (25° C.)

Yield: 85%

EXAMPLE 13

Production of 4-methyl-5-phenylsulfonylmethyl-1,2,3-thiadiazole (Compound No. 211)

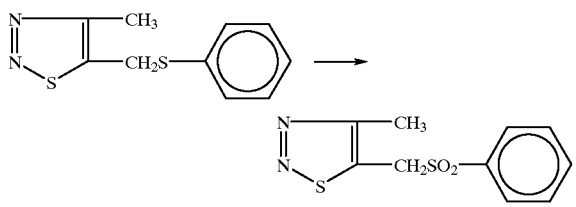

In 5.0 ml of methylene chloride was dissolved 0.20 g (0.99 mmol) of 4-methyl-5-phenylthiomethyl-1,2,3-thiadiazole. Then, 0.40 g (2.3 mmol) of m-chloroperbenzoic acid was added to the solution obtained above, and was stirred for 20 hours at room temperature. Then, an aqueous solution of sodium hydrogen sulfite was added to the reaction mixture to stop the reaction, the objective product was extracted with ethyl acetate, the organic layer was washed with a saturated aqueous solution of sodium hydrogen carbonate, the solvent was distilled off under reduced pressure, and the residue was purified by silica gel column chromatography using 2:1 mixture of n-hexane and ethyl acetate. Thus, 0.23 g of the objective compound was obtained.

Property: m.p. 118° C.

Yield: 100%

EXAMPLE 14

Production of 5-aminomethyl-4-methyl-1,2,3-thiadiazole hydrochloride (Compound No. 220)

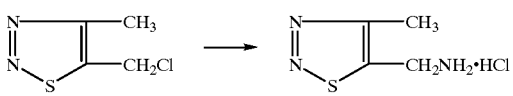

To 50 ml of acetonitrile were added 7.0 g (47 mmol) of 5-chloromethyl-4-methyl-1,2,3-thiadiazole and 9.0 g (94 mmol) of sodium formimide. After stirring the resulting mixture for 16 hours with heating under reflux, the reaction mixture was cooled to the room temperature, a saturated aqueous solution of sodium chloride was added, the objective product was extracted with ethyl acetate, the organic layer was washed with water and dried, and the solvent was distilled off under reduced pressure. Then, while stirring the resulting crystalline product together with 40 ml of water, 30 ml of concentrated hydrochloric acid was added. After ten minutes, water and hydrochloric acid were distilled off, and the residue was washed with ethyl acetate. Thus, 6.6 g of the objective compound was obtained.

Property: m.p. >250° C.

Yield: 77%

EXAMPLE 15

Production of 5-(N,N-diallylamino)methyl-4-methyl-1,2,3-thiadiazole (Compound No. 222)

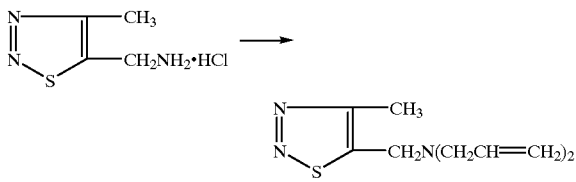

To 15 ml of acetone were added 0.50 g (3.0 mmol) of 5-aminomethyl-4-methyl-1,2,3-thiadiazole hydrochloride, 1.10 g (9.0 mmol) of allyl bromide and 2.1 g (15 mmol) of potassium carbonate. The resulting mixture was stirred for 20 hours with heating under reflux. After the reaction was completed, the reaction mixture was filtered to remove the precipitated matter, the solvent was distilled off under reduced pressure, and the residue was purified by silica gel column chromatography using 3:1 mixture of n-hexane and ethyl acetate. Thus, 0.42 g of the objective compound was obtained.

Property: Pasty product

Yield: 67%

H-NMR [CDCl$_3$/TMS, β value (ppm)] 2.61 (s, 3 H), 3.10–3.12 (m, 4 H), 3.80 (s, 2 H), 5.16–5.24 (m, 4 H), 5.78–5.89 (m, 2 H)

EXAMPLE 16

Production of methyl (E)-3-(4-methyl-1,2,3-thiadiazol-5-yl)-2-propenate (Compound No. 338) and methyl (Z)-3-(4-methyl-1,2,3-thiadiazol-5-yl)-2-propenate (Compound No. 341)

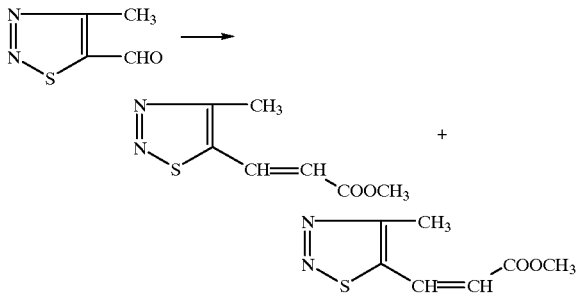

To 0.40 g (3.1 mmol) of 4-methyl-1,2,3-thiadiazol-5-carbaldehyde dissolved in tetrahydrofuran was added 1.1 g (3.4 mmol) of methyltriphenylphos phoranylidensacetate. The solution thus obtained was stirred for 16 hours at room temperature. After the reaction was completed, the reaction mixture was cooled to room temperature, a saturated aqueous solution of sodium chloride was added, and the objective product was extracted with ethyl acetate. The organic layer was washed with water and dried, the solvent was distilled off under reduced pressure, and the residue was purified by silica gel column chromatography using 5:1 mixture of n-hexane and ethyl acetate. Thus, the E-compound and the Z-compound, both the objective compounds, were obtained in yields of 0.49 g and 0.05 g, respectively.

Property: E-compound m.p. 70° C., Yield 90%

Z-compound m.p. 80–85° C., Yield 10%

EXAMPLE 17

Production of ethyl 2-cyano-3-(4-methyl-1,2,3-thiadiazol-5-yl)-2-propenate (Compound No. 346)

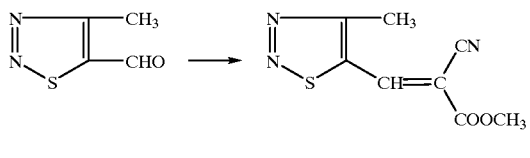

To 50 ml of toluene were added 1.5 g (12 mmol) of 4-methyl-1,2,3-thiadiazole-5-carbaldehyde, 1.5 g (13 mmol) of ethyl cyanoacetate, 0.40 g (6.0 mmol) of pyrrolidine and 0.20 g (1.2 mmol) of tosylic acid. In a reactor equipped with a Dean-Stark dehydrating apparatus, the mixture obtained above was stirred for 2 hours with heating under reflux. After the reaction was completed, a saturated aqueous solution of sodium Achloride was added to the reaction mixture, the objective product was extracted with ethyl acetate, the organic layer was washed successively with dilute hydrochloric acid, saturated aqueous solution of sodium hydrogen carbonate and saturated aqueous solution of sodium chloride, the solvent was distilled off under reduced pressure, and the residue was purified by silica gel column chromatography using 3:1 mixture of n-hexane and ethyl acetate. Thus, 0.73 g of the objective compound was obtained.

Property: Pasty product,

Yield: 30%

H-NMR [CDCl$_3$/TMS, β value (ppm)] 1.41 (t, 3 H), 2.90 (s, 3 H), 4.20 (q, 2 H), 8.34 (s, 1 H)

EXAMPLE 18

Production of 4-phenyl-3,4,5,6-tetrahydropyrimidin-2-yl-1,2,3-thiadiazole (Compound No. 368)

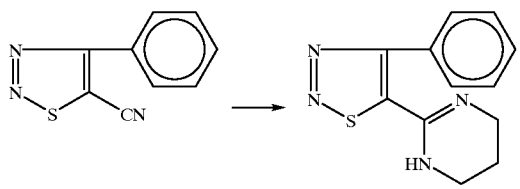

In 10 ml of ethanol were dissolved 0.95 g (5.0 immol) of 4-phenyl-1,2,3-thiadiazole-5-carbonitrile and 3.8 g (50 mmol) of 1,3-propanediamine. After adding 0.05 g of sodium ethoxide, the solution thus obtained was stirred for 8 hours with heating under reflux. After the reaction was completed, the reaction mixture was cooled to room temperature, the solvent was distilled off under reduced pressure, and the objective product was extracted with ethyl acetate. The organic layer was concentrated under reduced pressure, and the oily product thus obtained was recrystallized from a small quantity of ethyl acetate to obtain 0.68 g of the objective compound.

Property: m.p. 158° C.

Yield: 55%

EXAMPLE 19

Production of methyl 2-(4-phenyl-1,2,3-thiadiazol-5-yl)thiazole-4-carboxylate (Compound No. 372)

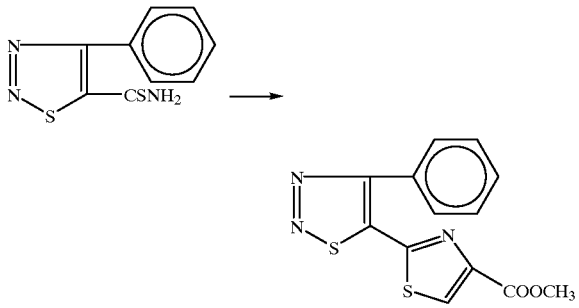

In 20 ml of chlorobenzene were dissolved 1.1 g (5.0 mmol) of 4-phenyl-1,2,3-thiadiazole-5-carbothioamide and 0.92 g (5.0 mmol) of methyl bromopyruvate. The solution thus obtained was stirred for 3 hours with heating under reflux. After the reaction was completed, the reaction mixture was cooled to room temperature, a saturated aqueous solution of sodium hydrogen carbonate was added thereto, and the objective product was extracted with ethyl acetate. The solvent was distilled off from the extract solution under a reduced pressure, and the residue was purified by silica gel column chromatography using 3:1 mixture of n-hexane and ethyl acetate. Thus, 0.74 g of the objective compound was obtained.

Property: m.p. 124° C.

Yield: 41%

Next, typical formulation examples and test examples of the present invention are mentioned below.

In the formulation examples, the term "parts" means "parts by weight".

Formulation Example 1

| | |
|---|---|
| The compound shown in Table 1 | 50 parts |
| Xylene | 40 parts |
| Mixture of polyoxyethylene nonyl-phenyl ether and calcium alkyl-benzenesulfonate | 10 parts |

The ingredients mentioned above are uniformly mixed and dissolved together to prepare an emulsifiable concentrate.

Formulation Example 2

| | |
|---|---|
| The compound shown in Table 1 | 3 parts |
| Clay powder | 82 parts |
| Diatomaceous earth powder | 15 parts |

The ingredients mentioned above are uniformly mixed together and pulverized to prepare a dust.

Formulation Example 3

| | |
|---|---|
| The compound shown in Table 1 | 5 parts |
| Powdery mixture of bentonite and clay | 90 parts |
| Calcium ligninsulfonate | 5 parts |

The ingredient mentioned above are kneaded together with a proper quantity of water, and then granulated and dried to prepare a granular composition.

Formulation Example 4

| | |
|---|---|
| The compound shown in Table 1 | 20 parts |
| Kaolinite and synthetic high-dispersion silicic acid | 75 parts |
| Mixture of polyoxyethylene nonylphenyl ether and calcium alkylbenzenesulfonate | 5 parts |

The ingredients mentioned above are uniformly mixed together and pulverized to prepare a wettable powder.

Test Example 1: Rice blast-controlling test by submerged application

A chemical agent containing the compound shown in Table 1 as an active ingredient was applied to paddy rice plants of the 5- to 6-leaved stage, cultivated in 1/10000 are pots, by the method of submerged application at a dosage of 200 g/10 ares as expressed in terms of active ingredient. After standing in a greenhouse for a week, the plants were inoculated with a spore suspension of rice blast fungus (*Pyricularia oryzae*) by the method of spraying.

After the inoculation, the plants were allowed to stand in a moist chamber for one day and then in a greenhouse for 6 days to cause the disease sufficiently. Then, lesions on each leaf were counted and compared with those in the untreated plot, from which the controlling degree was calculated, whereby the effect was judged according to the following criterion:

| Effect | Controlling degree (%) |
|---|---|
| A | 100–95 |
| B | 94–85 |
| C | 84–60 |
| D | 59–0 |

The results of the above test demonstrate that the compounds listed in Table 1 were found to have a marked blast-controlling activity. Of these compounds, the following were rated C or higher: Compound Nos. 7, 17–19, 21, 24, 35, 36, 60, 62, 66–69, 77, 83, 84, 87–89, 91, 93–100, 102, 104–106, 109, 129, 150, 162, 180, 209, 220–222, 229, 239, 260, 263, 273, 295, 299, 327, 338, 341, 342, 346, 365, 367, 369, 371 and 376. Especially, the following exhibited so excellent a blast-controlling activity as rated A: Compound Nos. 7, 37, 88, 89, 91, 104, 105, 109, 129, 150, 220, 221, 222, 239, 260, 263, 273, 299, 327, 342, 367 and 371.

What is claimed is:

1. An agrohorticultural disease controller comprising as the active ingredient a 1,2,3-thiadiazole derivative represented by the following general formula (I) or a salt thereof:

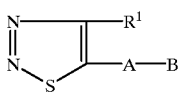

(I)

wherein $R^1$ represents hydrogen atom, $C_1$–$C_8$ alkyl group, halo $C_1$–$C_4$ alkyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group and $C_1$–$C_4$ alkoxycarbonyl group, 5- or 6heterocycle containing 1 to 3 same or different heteroatoms selected from oxygen atom, nitrogen atom and sulfur atom, or substituted 5- or 6-membered heterocycle containing 1 to 3 same or different heteroatoms selected from oxygen atom, nitrogen atom and sulfur atom, or substituted 5- or 6-membered heterocycle containing 1 to 3 same or different heteroatoms selected from oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups;

A represents a group of the following formula:

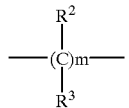

(wherein $R^2$ and $R^{3,}$ same or different, represent hydrogen atom, halogen atom, cyano group, formyl group, $C_1$–$C_4$ alkyl group, $C_1$–$C_4$ alkoxy group, $C_1$–$C_4$ alkylthio group, $C_1$–$C_4$ alkylsulfinyl group, $C_1$–$C_4$ alkylsulfonyl group, $C_1$–$C_4$ alkylcarbonyl group, $C_1$–$C_4$ alkoxycarbonyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group and $C_1$–$C_4$ alkoxycarbonyl group, phenylcarbonyl group, or substituted phenylcarbonyl group having, on the ring thereof, 1 to 5 same or different substituents selected from the group consisting of halogen atom, hydroxyl group, cyano group, $C_1$–$C_4$ alkyl group and $C_1$–$C_4$ alkoxycarbonyl group; further, $R^2$ and $R^3$ may be taken conjointly to form a 3- to 7-membered ring including a $C_2$–$C_6$ alkylene group which may be intercepted by —O—,
—S(O)$_n$— in which n is an integer of 0 to 2,
—CO— or
—NR$^8$— in which $R^8$ represents hydrogen atom, formyl group, $C_1$–$C_8$ alkyl group, halo $C_1$–$C_4$ alkyl group, $C_2$–$C_4$ alkenyl group, halo $C_2$–$C_4$ alkenyl group, $C_2$–$C_4$ alkynyl group, halo $C_2$–$C_4$ alkynyl group, $C_1$–$C_4$ alkylthio group, $C_1$–$C_4$ alkylsulfinyl group, $C_1$–$C_4$ alkylsulfonyl group, $C_1$–$C_4$ alkylcarbonyl group, $C_1$–$C_4$ alkoxycarbonyl group, carbamoyl group, substituted carbamoyl group having 1 or 2 same or different substituents selected from the group consisting of $C_1$–$C_4$ alkyl group and phenyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenyl $C_1$–$C_4$ alkyl group, substituted phenyl $C_1$–$C_4$ alkyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenylcarbonyl group, or substituted phenylcarbonyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group; and said 3- to 7-membered ring may be substituted by one or more same or different substituents selected from the group consisting of halogen atom and $C_1$–$C_4$ alkyl group; and m represents an integer of 0 to 4), or

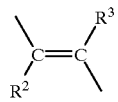

in which $R^2$ and $R^3$ are as defined above,

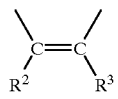

in which $R^2$ and $R^3$ are as defined above,

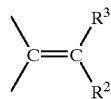

in which $R^2$ and $R^3$ are as defined above; and
in the case that m is 0 in the definition of A, B represents, 5- or 6-membered heterocycle having 1 to 3 same or different hetero atoms selected from the group consisting of oxygen atom, nitrogen atom and sulfur atom, substituted 5- or 6-heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different $C_1$–$C_4$ alkyl or phenyl groups, carbamoyl group, substituted carbamoyl group having 1 or 2 $C_1$–$C_4$ alkyl or phenyl groups, carbamoyl $C_1$–$C_4$ alkyl group and substituted carbamoyl $C_1$–$C_4$ alkyl group having 1 or 2 same or different $C_1$–$C_4$ alkyl or phenyl groups, or $$—C(=X)R^4$$

(in which $R^4$ represents hydrogen atom, $C_1$–$C_8$ alkyl group, halo $C_1$–$C_4$ alkyl group, $C_2$–$C_4$ alkenyl group, halo $C_2$–$C_4$ alkenyl group, $C_2$–$C_4$ alkynyl group, halo $C_2$–$C_4$ alkynyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenyl $C_1$–$C_4$ alkyl group, substituted phenyl $C_1$–$C_4$ alkyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, 5- or 6-membered heterocycle containing 1 to 3 same or different hetero atoms selected from the group consisting of oxygen atom, nitrogen atom and sulfur atom, or substituted 5- or 6 membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl group and phenyl group, carbamoyl group, substituted carbamoyl group having 1 or 2 same or different substituents selected from the group consisting of $C_1$–$C_4$ alkyl group and phenyl group, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl group and phenyl group, and X represents O, S, N—$R^6$ in which $R^6$ is as defined later, NO—$R^6$ in which $R^6$ is as defined later, N($\leq$O)—$R^6$ in which $R^6$ is as defined later, NN($R^6$)$R^7$ in which $R^6$ and $R^7$ are as defined later, or NN=C($R^6$)$R^7$ (in which $R^6$ and $R^7$, same or different, represent hydrogen atom, halogen atom, formyl group, $C_1$–$C_4$ alkyl group, $C_2$–$C_4$ alkenyl group, $C_2$–$C_4$ alkynyl group, $C_1$–$C_4$ alkylsulfonyl group, halo $C_1$–$C_4$ alkylsulfonyl group, $C_1$–$C_{20}$ alkylcarbonyl group, $C_1$–$C_4$ alkoxycarbonyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group, amino group and $C_1$–$C_4$ alkoxycarbonyl group, phenyl $C_1$–$C_4$ alkyl group, substituted phenyl $C_1$–$C_4$ alkyl group having, on the ring thereof, 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group, amino group and $C_1$–$C_4$ alkoxycarbonyl group, phenylcarbonyl group, substituted phenylcarbonyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group and $C_1$–$C_4$ alkoxycarbonyl group, carbamoyl group, substituted carbamoyl group having 1 or 2 same or different substituents selected from the group consisting of $C_1$–$C_4$ alkyl group, phenyl group and substituted phenyl group having, on the ring thereof, 1 to 5 same or different substituents selected from the group consisting of halogen atom, $C_1$–$C_4$ alkyl group, halo $C_1$–$C_4$ alkyl group, $C_1$–$C_4$ alkoxy group and halo $C_1$–$C_4$ alkoxy group, phenylsulfonyl group, substituted phenylsulfonyl group having 1 to 5 same or different substituents selected from the group consisting of halogen atom, hydroxyl group, cyano group, nitro group, $C_1$–$C_4$ alkyl group, $C_1$–$C_4$ alkoxy group and $C_1$–$C_4$ alkoxycarbonyl group, thiocarbamoyl group, substituted thiocarbamoyl group substituted by same or different $C_1$–$C_4$ alkyl or phenyl group, $C_1$–$C_4$ alkoxy carbonimidoyl group, substituted $C_1$–$C_4$ alkoxy carbonimidoyl group having, on the nitrogen atom thereof, same or different substituents selected from the group consisting of $C_1$–$C_4$ alkyl and phenyl groups, $C_1$–$C_4$ alkylthio carbonimidoyl group, substituted $C_1$–$C_4$ alkylthio carbonimidoyl group having, on the nitrogen atom thereof, same or different substituents selected from the group consisting of $C_1$–$C_4$ alkyl and phenyl groups, $C_1$–$C_4$ alkylsulfinyl carbonimidoyl group, substituted $C_1$–$C_4$ alkylsulfinyl carbonimidoyl group having, on the nitrogen atom thereof, same or different substituents selected from the group consisting of $C_1$–$C_4$ alkyl and phenyl groups, $C_1$–$C_4$ alkylsulfonyl carbonimidoyl group, substituted $C_1$–$C_4$ alkylsulfonyl carbonimidoyl group having, on the nitrogen atom thereof, same or different substituents selected from the group consisting of $C_1$–$C_4$ alkyl and phenyl groups, amidino group, substituted amidino group having same or different substituents selected from the group consisting of $C_1$–$C_6$ alkyl and phenyl groups, 5- or 6-membered heterocycle containing 1 to 3 same or different hetero atoms selected from the group consisting of oxygen atom, nitrogen atom and sulfur atom, or substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups; and $R^6$ and $R^7$ may be taken conjointly to form a 3- to 7-membered ring including a $C_2$–$C_6$ alkylene group which may be intercepted by

—O—,

—S(O)$_n$— in which n is as defined above,

—CO—, or

—N$R^8$— in which $R^8$ is as defined above, and said 3- to 7-membered ring may have same or different substituents selected from the group consisting of halogen atom and $C_1$–$C_4$ alkyl group)); and in cases where m is 1 or greater, B represents hydrogen atom, halogen atom, cyano group, 5- or 6-membered heterocycle containing 1 to 3 same or different hetero atoms selected from the group consisting of oxygen atom, nitrogen atom and sulfur atom, substituted 5- or 6-membered heterocycle containing 1 to 3 same or different hetero atoms selected from the group consisting of oxygen atom, nitrogen atom and sulfur atom and having 1 to 3 same or different substituents selected from the group consisting of halogen atom, hydroxyl group, cyano group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups, $$—C(=X)\ R^5$$

(in which X is as defined above; and $R^5$ represents hydrogen atom, $C_1$–$C_8$ alkyl group, halo $C_1$–$C_4$ alkyl group, $C_2$–$C_4$ alkenyl group, halo $C_2$–$C_4$ alkenyl group, $C_2$–$C_4$ alkynyl group, halo $C_2$–$C_4$ alkynyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, phenyl $C_1$–$C_4$ alkyl group, substituted phenyl $C_1$–$C_4$ alkyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, 5- to 6-membered heterocycle containing 1 to 3 same or different hetero atoms selected from the group consisting of oxygen atom, nitrogen atom and sulfur atom, substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups, O—$R^6$ in which R is as defined above, S(O)$_n$—$R^6$ in which n and $R^6$ are as defined above, or N($R^6$)$R^7$ in which $R^6$ and $R^7$ are as defined above),

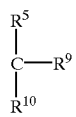

(wherein $R^5$ is as defined above; and $R^9$ and $R^{10}$, same or different, represent formyl group, $C_1$–$C_4$ alkylcarbonyl group, $C_1$–$C_4$ alkoxycarbonyl group, phenylcarbonyl group, or substituted phenylcarbonyl group having, on the ring thereof, 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group; firther, $R^9$ and $R^{10}$ may be taken conjointly to form a 3- to 7-membered ring including a $C_2$ to $C_6$ alkylene group which may be intercepted by

—O—,

—S(O)$_n$— in which n is as defined above,

—CO—, or

—N($R^8$)— in which $R^8$ is as defined above, and said 3- to 7-membered ring may have one or more same or different substituents selected from the group consisting of halogen atom and $C_1$–$C_4$ alkyl group), O—$R^6$ in which $R^6$ is as defined above, S(O)$_n$—$R_6$ in which $R_6$ and n are as defined above, N($R^6$)$R^7$ in which $R^6$ and $R^7$ are as defined above, N=C($R^6$)$R^7$ in which $R^6$ and $R^7$ are as defined above, or ON=C($R^6$)$R^7$ in which $R^6$ and $R^7$ are as defined above.

2. An agrohorticultural disease controller comprising as the active ingredient a 1,2,3-thiadiazole derivative or a salt thereof, wherein $R^1$ represents hydrogen atom, $C_1$–$C_8$ alkyl group or halo $C_1$–$C_4$ alkyl group;

A represents the following formula:

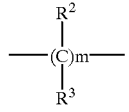

(wherein $R^2$ and $R^3$, same or different, represent hydrogen atom, halogen atom, cyano group, formyl group, $C_1$–$C_4$ alkyl group, $C_1$–$C_4$ alkoxy group, $C_1$–$C_4$ alkylthio group, $C_1$–$C_4$ alkylsulfinyl group, $C_1$–$C_4$ alkylsulfonyl group, $C_1$–$C_4$ alkylcarbonyl group, $C_1$–$C_4$ alkoxycarbonyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_4$ alkyl group, Cl-$C_4$ alkoxy group, halo $C_1$–$C_4$ alkoxy group and $C_1$–$C_4$ alkoxycarbonyl group, phenylcarbonyl group, or substituted phenylcarbonyl group having, on the ring thereof, 1 to 5 same or different substituents selected from the group consisting of halogen atom, hydroxyl group, cyano group, $C_1$–$C_4$ alkyl group and $C_1$–$C_4$ alkoxycarbonyl group; and m represents an integer of 0 to 4) and in the case that m is 0 in the definition of A, B represents, 5- or 6-membered heterocycle containing 1 to 3 same or different hetero atoms selected from the group consisting of oxygen atom, nitrogen atom and sulfur atom, substituted 5- or 6-membered heterocycle containing 1 to 3 same or different hetero atoms selected from the group consisting of oxygen atom, nitrogen atom and sulfur atom and having 1 to 4 same or different substituents selected from the group consisting of halogen atom, cyano group, hydroxyl group, mercapto group, $C_1$–$C_4$ alkyl group, $C_1$–$C_4$ alkoxy group, $C_1$–$C_4$ alkylthio group, formyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, substituted amino group having 1 or 2 same or different substituents selected from the group consisting of $C_1$–$C_4$ alkyl and phenyl groups, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups, or

—C(=X)R$^4$ (in which R$^4$ represents hydrogen atom, $C_1$–$C_8$ alkyl group, halo $C_1$–$C_4$ alkyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ aLkoxycarbonyl group, or 5- or 6-membered heterocycle containing 1 to 3 same or different hetero atoms selected from the group consisting of oxygen atom, nitrogen atom and sulfuir atom; and X represents O, S, NO—R$^6$ in which R$^6$ is as defined later, or NN(R$^6$)(R$^7$)(in which R$^6$ and R$^7$, same or different, represent hydrogen atom, halogen atom, formyl group, $C_1$–$C_4$ alkyl group, $C_2$–$C_4$ alkenyl group, $C_2$–$C_4$ alkynyl group, $C_1$–$C_4$ alkylsulfonyl group, halo $C_1$–$C_4$ alkylsulfonyl group, $C_1$–$C_{20}$ alkylcarbonyl group, $C_1$–$C_4$ alkoxycarbonyl group, phenyl group, substituted phenyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group, amino group and $C_1$–$C_4$ alkoxycarbonyl group, phenyl $C_1$–$C_4$ alkyl group, substituted phenyl $C_1$–$C_4$ alkyl group having, on the ring thereof, 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group, amino group and $C_1$–$C_4$ alkoxycarbonyl group, phenylcarbonyl group, substituted phenylcarbonyl group having 1 to 5 same or different substituents selected from the group consisting of halogen atom, hydroxyl group, cyano group, nitro group, $C_1$–$C_4$ alkyl group, halo $C_1$–$C_4$ alkyl group, $C_1$–$C_4$ alkoxy group, halo $C_1$–$C_4$ alkoxy group and $C_1$–$C_4$ alkoxycarbonyl group, carbamoyl group, substituted carbamoyl group having 1 or 2 same or different substituents selected from the group consisting of $C_1$–$C_4$ alkyl group, phenyl group and substituted phenyl group having 1 to 5 same or different substituents selected from the group consisting of halogen atom, $C_1$–$C_4$ alkyl group, halo $C_1$–$C_4$ alkyl group, $C_1$–$C_4$ alkoxy group and halo $C_1$–$C_4$ alkoxy group, phenylsulfonyl group, substituted phenylsulfonyl group having 1 to 5 same or different substituents selected from the group consisting of halogen atom, hydroxyl group, cyano group, nitro group, $C_1$–$C_4$ alkyl group, $C_1$–$C_4$ alkoxy group and $C_1$–$C_4$ alkoxycarbonyl group, thiocarbamoyl group, substituted thiocarbamoyl group substituted by same or different $C_1$–$C_4$ alkyl or phenyl group, $C_1$–$C_4$ alkoxy carbonimidoyl group, substituted $C_1$–$C_4$ alkoxy carbonimidoyl group having, on the nitrogen atom thereof, same or different substituents selected from the group consisting of $C_1$–$C_4$ alkyl and phenyl groups, $C_1$–$C_4$ alkylthio carbonimidoyl group, substituted $C_1$–$C_4$ alkylthio carbonimidoyl group having, on the nitrogen atom thereof, same or different substituents selected from the group consisting of $C_1$–$C_4$ alkyl and phenyl groups, $C_1$–$C_4$ alkylsulfinyl carbonimidoyl group, substituted $C_1$–$C_4$ alkylsulfinyl carbonimidoyl group having, on the nitrogen atom thereof, same or different substituents selected from the group consisting of $C_1$–$C_4$ alkyl and phenyl groups, $C_1$–$C_4$ alkylsulfonyl carbonimidoyl group, substituted $C_1$–$C_4$ alkylsulfonyl carbonimidoyl group having, on the nitrogen atom thereof, same or different substituents selected from the group consisting of $C_1$–$C_4$ alkyl and phenyl groups, amidino group, substituted amidino group having same or different substituents selected from the group consisting of $C_1$–$C_6$ alkyl and phenyl groups, or 5- or 6-membered heterocycle containing 1 to 3 same or different hetero atoms selected from the group consisting of oxygen atom, nitrogen atom and sulfur atom)); and in cases where m is 1 or greater, B represents hydrogen atom, halogen atom, cyano group, 5- or 6-membered heterocycle containing 1 to 3 same or different hetero atoms selected from the group consisting of oxygen atom, nitrogen atom and sulfuir atom, substituted 5- or 6-membered heterocycle containing 1 to 3 same or different hetero atoms selected from the group consisting of oxygen atom, nitrogen atom and sulfur atom and having 1 to 3 same or different substituents selected from the group consisting of halogen atom, hydroxyl group, cyano group, mercapto group, $C_1$–$C_4$ alkyl group, $C_1$–$C_4$ alkoxy group, $C_1$–$C_4$ alkylthio group, carbonyl group, carboxyl group, carboxy $C_1$–$C_4$ alkyl group, $C_1$–$C_4$ alkoxycarbonyl group, $C_1$–$C_4$ alkoxycarbonyl $C_1$–$C_4$ alkyl group, amino group, carbamoyl group, substituted carbamoyl group having 1 or 2 same or different substituents selected from the group consisting of $C_1$–$C_4$ alkyl and phenyl groups, carbamoyl $C_1$–$C_4$ alkyl group, and substituted carbamoyl $C_1$–$C_4$ alkyl group having 1 or 2 same or different substituents selected from the group consisting of $C_1$–$C_4$ alkyl and phenyl groups,

—C(=X) R$^5$ (in which X is as defined above; and R$^5$ represents hydrogen atom, $C_1$–$C_8$ alkyl group, halo $C_1$–$C_4$ alkyl group, phenyl group, substituted phenyl group having 1 to 5 same or different substituents selected from the group consisting of halogen atom, cyano group, hydroxyl group, $C_1$–$C_4$ alkyl group, $C_1$–$C_4$ alkoxy group and $C_1$–$C_4$ alkoxycarbonyl group, 5- or 6-membered heterocycle having 1 to 3 same or different hetero atoms selected from the group consisting of oxygen atom, nitrogen atom and sulfur atom, O—R$^6$ in which R$^6$ is as defined above, S(O)$_n$—R$^6$ in which n and R$^6$ are as defined above, or N(R$^6$)R$^7$ in which R$^6$ and R$^7$ are as defined above), O—R$^6$ in which R$^6$ is as defined above, S(O)$_n$—R$^6$ in which n and R$^6$ are as defined above, N(R$^6$)R$^7$ in which R$^6$ and R$^7$ are as defined above, N=C(R$^6$)R$^7$ in which R$^6$ and R$^7$ are as defined above, or ON=C(R$^6$)R$^7$ in which R$^6$ and R$^7$ are as defined above.

3. A method for controlling a plant disease which comprises treating a plant on which occurrence of plant disease is undesirable with an effective quantity of the agrohorticultural disease controller according to claim 1.

4. A method for controlling a plant disease which comprises treating a plant on which occurrence of plant disease is undesirable with an effective quantity of the agrohorticultural disease controller according to claim 2.

* * * * *